United States Patent
Kostic et al.

(10) Patent No.: US 10,730,948 B2
(45) Date of Patent: *Aug. 4, 2020

(54) METHODS FOR TREATING EOSINOPHILIC ESOPHAGITIS BY ADMINISTERING AN IL-4R INHIBITOR

(71) Applicant: Regeneron Pharmaceuticals, Inc., Tarrytown, NY (US)

(72) Inventors: Ana Kostic, New York, NY (US); Ludmila Kelly, Tarrytown, NY (US); Xia Liu, Hopewell Junction, NY (US); Brendan J. Classon, Seattle, WA (US); Allen Radin, New York, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/017,664

(22) Filed: Feb. 7, 2016

(65) Prior Publication Data

US 2016/0152718 A1 Jun. 2, 2016

Related U.S. Application Data

(63) Continuation of application No. 14/328,336, filed on Jul. 10, 2014.

(60) Provisional application No. 61/844,978, filed on Jul. 11, 2013.

(51) Int. Cl.
| | | |
|---|---|---|
| *A61K 9/00* | (2006.01) | |
| *A61K 31/56* | (2006.01) | |
| *A61K 39/00* | (2006.01) | |
| *A61K 45/06* | (2006.01) | |
| *C07K 16/28* | (2006.01) | |
| *A61K 39/395* | (2006.01) | |

(52) U.S. Cl.
CPC ........ *C07K 16/2866* (2013.01); *A61K 9/0019* (2013.01); *A61K 31/56* (2013.01); *A61K 39/3955* (2013.01); *A61K 45/06* (2013.01); *A61K 2039/505* (2013.01); *A61K 2039/54* (2013.01); *A61K 2039/545* (2013.01); *A61K 2039/577* (2013.01); *C07K 2317/21* (2013.01); *C07K 2317/565* (2013.01); *C07K 2317/76* (2013.01); *C07K 2318/00* (2013.01)

(58) Field of Classification Search
CPC ............ C07K 16/2866; C07K 2318/00; C07K 2317/565; C07K 2317/21; C07K 2317/76; A61K 9/0019; A61K 45/06; A61K 31/56; A61K 39/3955; A61K 2039/577; A61K 2039/54; A61K 2039/545; A61K 2039/505
See application file for complete search history.

(56) References Cited

U.S. PATENT DOCUMENTS

| | | |
|---|---|---|
| 5,599,905 A | 2/1997 | Mosley |
| 5,714,146 A | 2/1998 | Lewis |
| 5,717,072 A | 2/1998 | Mosley |
| 5,856,296 A | 1/1999 | Mosley |
| 5,985,280 A | 11/1999 | Ritter |
| 6,156,877 A | 12/2000 | Ritter |
| 6,391,581 B1 | 5/2002 | Mosley |
| 6,548,655 B1 | 4/2003 | Mosley |
| 6,716,587 B2 | 4/2004 | Mosley |
| 7,141,653 B2 | 11/2006 | Greenfeder |
| 7,186,809 B2 | 3/2007 | Pluenneke |
| 7,317,090 B2 | 1/2008 | Mosley |
| 7,422,742 B2 | 9/2008 | Greenfeder |
| 7,531,169 B2 | 5/2009 | Singh |
| 7,605,237 B2 | 10/2009 | Stevens |
| 7,608,693 B2 | 10/2009 | Martin |
| 7,794,717 B2 | 9/2010 | Stevens |
| 8,030,003 B2 | 10/2011 | Rothenberg |
| 8,075,887 B2 | 12/2011 | Martin |
| 8,075,897 B2 | 12/2011 | Spertini |
| 8,092,802 B2 | 1/2012 | Stevens |
| 8,092,804 B2 | 1/2012 | Eriksson et al. |
| 8,252,284 B2 | 8/2012 | Singh |
| 8,324,192 B2 | 12/2012 | Dohil |
| 8,337,839 B2 | 12/2012 | Martin |
| 8,338,135 B2 | 12/2012 | Stevens |
| 8,497,528 B2 | 7/2013 | Lee |
| 8,604,171 B2 | 12/2013 | Singh |
| 8,637,239 B2 | 1/2014 | Furuta |
| 9,290,574 B2 | 3/2016 | Kostic |
| 10,485,844 B2 | 11/2019 | Radin |
| 2003/0103938 A1 | 6/2003 | Jinquan |

(Continued)

FOREIGN PATENT DOCUMENTS

| | | |
|---|---|---|
| EP | 0604693 | 7/1994 |
| EP | 0367566 | 5/1997 |

(Continued)

OTHER PUBLICATIONS

Brown-Whitehorn TF and Spergel JM. Expert Rev. Clin. Immunol. 6(1):101-115. Jan. 1, 2010. Available online at—doi: 10.1586/eci.09.74.*

(Continued)

*Primary Examiner* — Robert S Landsman

(74) *Attorney, Agent, or Firm* — Merchant & Gould P.C.

(57) ABSTRACT

The present invention provides methods for treating, preventing or reducing the severity of eosinophilic esophagitis. The methods of the present invention comprise administering to a subject in need thereof a therapeutic composition comprising an interleukin-4 receptor (IL-4Rα) inhibitor such as an anti-IL-4Rα antibody.

20 Claims, 4 Drawing Sheets

Specification includes a Sequence Listing.

(56) References Cited

U.S. PATENT DOCUMENTS

| | | |
|---|---|---|
| 2003/0113387 A1 | 6/2003 | Tsuchida |
| 2003/0124121 A1 | 7/2003 | Pluenneke |
| 2005/0031609 A1 | 2/2005 | Hultsch |
| 2005/0074462 A1 | 4/2005 | Holmgren |
| 2005/0118176 A1 | 6/2005 | Mosley |
| 2005/0255532 A1 | 11/2005 | Ruben |
| 2005/0282181 A1 | 12/2005 | Yan |
| 2006/0013811 A1 | 1/2006 | Dina |
| 2007/0041976 A1 | 2/2007 | Pluenneke |
| 2007/0274996 A1 | 11/2007 | Carter |
| 2008/0054606 A1 | 5/2008 | Eriksson |
| 2009/0074793 A1 | 3/2009 | Martin |
| 2009/0098142 A1 | 4/2009 | Kasaian |
| 2009/0264392 A1 | 10/2009 | Warndahl |
| 2010/0047254 A1 | 2/2010 | Martin |
| 2011/0195500 A1 | 8/2011 | Rothenberg |
| 2012/0004205 A1 | 1/2012 | Rothenberg |
| 2012/0052072 A1 | 3/2012 | Martin |
| 2012/0164080 A1 | 6/2012 | Hill |
| 2012/0207815 A1 | 8/2012 | Benhamou |
| 2013/0052190 A1 | 2/2013 | Collins |
| 2013/0078675 A1 | 3/2013 | Martin |
| 2013/0324435 A1 | 12/2013 | Rothenberg |
| 2014/0072583 A1 | 3/2014 | Ardeleanu |
| 2014/0187523 A1 | 7/2014 | Dohil |
| 2014/0271681 A1 | 9/2014 | Martin |
| 2014/0356372 A1 | 12/2014 | Stahl |
| 2015/0017176 A1 | 1/2015 | Kostic |
| 2015/0185228 A1 | 7/2015 | Reisacher |
| 2015/0246973 A1 | 9/2015 | Graham |
| 2017/0333557 A1 | 11/2017 | Ardeleanu |
| 2018/0078603 A1 | 3/2018 | Radin |
| 2018/0094069 A1 | 4/2018 | Stahl |
| 2018/0094070 A1 | 4/2018 | Stahl |
| 2018/0179288 A1 | 6/2018 | Martin et al. |
| 2019/0040126 A1 | 2/2019 | Radin |
| 2019/0183973 A1 | 6/2019 | Hamilton |
| 2019/0345253 A1 | 11/2019 | Bansal |
| 2019/0367622 A1 | 12/2019 | Graham |

FOREIGN PATENT DOCUMENTS

| | | |
|---|---|---|
| EP | 1113818 B1 | 5/2006 |
| EP | 2022507 A1 | 2/2009 |
| EP | 1527100 | 7/2009 |
| JP | 05-246874 | 9/1993 |
| JP | 2006-131623 | 5/2006 |
| JP | 2016521713 A | 7/2016 |
| RU | 2162711 | 2/2001 |
| RU | 2453303 C1 | 6/2012 |
| WO | WO 92/19259 | 11/1992 |
| WO | WO 94/14975 | 7/1994 |
| WO | WO 2001/092340 | 12/2001 |
| WO | WO 2003/048083 | 6/2003 |
| WO | WO 2005/047331 | 5/2005 |
| WO | WO 2005/085284 | 9/2005 |
| WO | WO 2006/003407 | 1/2006 |
| WO | WO 2006/072564 | 7/2006 |
| WO | WO 2006/083390 | 8/2006 |
| WO | WO 2008/054606 | 5/2008 |
| WO | WO2009/124954 | 10/2009 |
| WO | WO 2010/053751 | 5/2010 |
| WO | WO 2010/065557 | 6/2010 |
| WO | WO 2010/120524 | 10/2010 |
| WO | WO 2011/026966 | 3/2011 |
| WO | WO 2012/047954 | 4/2012 |
| WO | WO 2012/094643 | 7/2012 |
| WO | WO 2012/177945 | 12/2012 |
| WO | WO 2013/051928 | 4/2013 |
| WO | 2013-088109 A1 | 6/2013 |
| WO | WO 2013/155010 | 10/2013 |
| WO | 2014/031610 | 2/2014 |
| WO | WO 2014/039461 | 3/2014 |
| WO | WO 2014/059178 | 4/2014 |
| WO | 2014/205365 | 12/2014 |
| WO | 2014197470 A1 | 12/2014 |
| WO | 2015/006571 | 1/2015 |
| WO | 2016077675 A1 | 5/2016 |
| WO | 2017/143270 | 8/2017 |
| WO | 2018/045130 | 3/2018 |
| WO | 2018/057776 | 3/2018 |

OTHER PUBLICATIONS

Yan BM and Shaffer EA. World J Gastroenterol. 12(15):2328-2334. Apr. 21, 2006. Available online at—http://www.wjgnet.com/1007-9327/12/2328.asp.*

Giusti, et al. (1987) Proc. Natl. Acad. Sci. 84:2926-2930, "Somatic diversification of S107 from an antiphosphocholine to anti-DNA autoantibody is due to a single base change in its heavy chain variable region".

Gussow and Seemann (1991) Methods in Enzymology 203:99-121, "Humanization of Monoclonal Antibodies".

Holm, et al. (2007) Molecular Immunology 44:1075-1084, "Functional mapping and single chain construction of the anti-cytokeratin 8 monoclonal antibody TS1".

MacCallum, et al. (1996) J. Mol. Biol. 262:732-745, "Antibody-antigen Interactions: Contact Analysis and Binding Site Topography".

Mariuzza, et al. (1987) Ann. Rev. Biophys. Biophys. Che. 16:139-159, "The Structural Basis of Antigen-Antibody Recognition".

Rudikoff, et al. (1982) Proc. Natl. Acad. Sci. 79:1979-1983, "Single amino acid substitution altering antigen-binding specificity".

Vajdos, et al. (2002) J. Mol. Biol. 320:415-428, "Comprehensive Functional Maps of the Antigen-binding Site of an Anti-ErbB2 Antibody Obtained with Shotgun Scanning Mutagenesis".

Winkler, et al. (2000) J. Immunol. 165(8):4505-4514, "Changing the Antigen Binding Specificity by Single Point Mutations of an Anti-p24 (HIV-1) Antibody".

Wu, et al. (1999) J. Mol. Biol. 294:151-162, "Humanization of a Murine Monoclonal Antibody by Simultaneous Optimization of Framework and CDR Residues".

De Pascalis, et al. (2002) J. Immunol. 169(6):3076-3084, "Grafting of "Abbreviated" Complementarity—Determining Regions Containing Specificity—Determining Residues Essential for Ligand Contact to Engineer a Less Immunogenic Humanized Monoclonal Antibody".

Chien, et al. (1989) Proc. Natl. Acad. Sci. 86:5532-5536, "Significant structural and functional change of an antigen-binding site by a distant amino acid substitution: Proposal of a structural mechanism".

Caldas, et al. (2003) Molecular Immunology 39:941-952, "Humanization of the anti-CD18 antibody 6.7: an unexpected effect of a framework residue in binding to antigen".

Casset, et al. (2003) Biochemical and Biophysical Research Communication 307:198-205, "A peptide mimetic of an anti-CD4 monoclonal antibody by rational design".

Abonia, et al., 2013, Journal of Allergy Clin Immunol, "High prevalence of eosinophilic esophagitis in patients with inherited connective tissue disorders".

Aceves, et al., 2009, Immunol Allergy Clin N Am 29 p. 197-211, "Relationships Between Eosinophilic Inflammation, Tissue Remodeling, and Fibrosis in Eosinophilic Esophagitis".

Assa'ad, et al., 2011, Gastroenterology 141:1593-1604, "An Antibody Against IL-5 Reduces Numbers of Esophageal Intraepithelial Eosinophils in Children with Eosinophilic Esophagitis".

Barnes, 2008, The Journal of Clinical Investigation 118(11):3546-3556, "The cytokine network in asthma and chronic obstructive pulmonary disease".

Beyer, et al., 2002, Journal of Allergy Clin Immunol 109(4):707-713, "Human milk-specific mucosal lymphocytes of the gastrointestinal tract display a $T_H2$ cytokine profile".

Bhardwaj and Ghaffari, 2012, Ann Allergy Asthma Immunol 109:155-159, "Biomarkers for eosinophilic esophagitis: a review".

Blanchard, et al., 2005, Clin Exp Allergy 35:1096-1103, "Inhibition of human interleukin-13-induced respiratory and oesophageal inflammation by anti-human-interleukin-13 antibody (CAT-354)".

(56) References Cited

OTHER PUBLICATIONS

Blanchard, et al., 2006, The Journal of Clinical Investigation 116(2), "Eotaxin-3 and a uniquely conserved gene-expression profile in eosinophilic esophagitis".
Blanchard, et al., 2007, Journal of Allergy Clin Immunol 120(6), "IL-13 involvement in eosinophilic esophagitis: Transcriptome analysis and reversibility with glucocorticoids".
Blanchard and Rothenberg, 2009, Immunol Allergy Clin N Am 29, p. 141-148, "Chemotactic Factors Associated with Eosinophilic Gastrointestinal Diseases".
Blanchard, et al., 2010, The Journal of Immunology, "Coordinate Interaction between IL-13 and Epithelial Differentiation Cluster Genes in Eosinophilic Esophagitis".
Blanchard, et al., 2011, J Allergy Clin Immunol, 127(1):208-217, "A striking local esophageal cytokine expression profile in eosinophilic esophagitis".
Chehade and Sampson, 2009, Immunol Allergy Clin N Am 29, p. 149-158, "The Role of Lymphocytes in Eosinophilic Gastrointestinal Disorders".
Dellon, 2013, Dig Dis Sci, "The Pathogenesis of Eosinophilic Esophagitis: Beyond the Eosinophil".
Desreumaux, et al., 1996, Gastroenterology 110:768-774, "Interleukin 3, Granulocyte-Macrophage Colony-Stimulating Factor, and Interleukin 5 in Eosinophilic Gastroenteritis".
Fillon, et al., 2009, Immunol Allergy Clin N Am 29, pp. 171-178, "Epithelial Function in Eosinophilic Gastrointestinal Diseases".
Foroughi, et al., 2007, J Allergy Clin Immunol 120(3):594-601, "Anti-IgE Treatment of Eosinophil Associated Gastrointestinal Disorders".
Franciosi and Liacouras, 2009, Immunol Allergy Clin N Am 29, pp. 19-27, "Eosinophilic Esophagitis".
Jyonouchi, et al., 2013, Basic Mechanisms in Allergic Disease, "Invariant Natural Killer T cells in children with Eosinophilic Esophagitis".
Katial, 2009, Immunol Allergy Clin N Am 29, pp. 119-127, "Biomarkers for Nononcologic Gastrointestinal Disease".
Kim, et al., 2004, J Allergy Clin Immunol 114(6):1449-1455, "Rebound eosinophilia after treatment of hypereosinophilic syndrome and eosinophilic gastroenteritis with monoclonal anti-IL-5 antibody SCH55700".
Konikoff, et al., 2006, Gastroenterology 131:1381-1391, "A Randomized, Double-Blind, Placebo-Controlled Trial of Fluticasone Propionate for Pediatric Eosinophilic Esophagitis".
Kottyan, et al., 2014, Nature Genetics, "Genome-wide association analysis of eosinophilic esophagitis provides insight into the tissue specificity of this allergic disease".
Liacouras, et al., 2011, J Allergy Clin Immunol 128(1), "Eosinophilic esophagitis: Updated consensus recommendations for children and adults".
Liu, et al, 1999, Gene Therapy, 6:1258-1266, "Hydrodynamics-based transfection in animals by systemic administration of plasmid DNA".
Lucendo and Sanchez-Cazalilla, 2012, Expert Rev. Clin. Immunol. 8(8):733-745, "Adult versus pediatric eosinophilic esophagitis: important differences and similarities for the clinician to understand".
Lwin, et al., 2011, Modern Pathology 24:556-563, "Eosinophilic gastritis: histopathological characterization and quantification of the normal gastric eosinophil content".
Masterson, et al., 2011, Curr Opin Gastroenterol. 27(6): 515-522, "Update on clinical and immunological features of eosinophilic gastrointestinal diseases".
Mishra, et al., 2001, J Clin. Invest. 107:83-90, "An etiological role for aeroallergens and eosinophils in experimental esophagitis".
Mishra, et al., 2002, The Journal of Immunology 168:2464-2469, "IL-5 Promotes Eosinophil Trafficking to the Esophagus".
Mishra and Rothenberg, 2003, Gastroenterology 125:1419-1427, "Intratracheal IL-13 Induces Eosinophilic Esophagitis by an IL-5, Eotaxin-1, and STAT6-Dependent Mechanism".

Niranjan, et al., 2013, Immunology and Cell Biology, pp. 1-8, "Pathogenesis of allergen-induced eosinophilic esophagitis is independent of interleukin (IL)-13".
Noel, et al., 2004, The New England Journal of Medicine 351:940-941, "Eosinophilic Esophagitis".
Novartis, 2013, QAX576 "A double blinded, randomized, placebo-controlled trial of intravenous QAX576 in the treatment of eosinophilic esophagitis".
Oh, et al., 2010, Eur Respir Rev 19(115):46-54, "Investigational therapeutics targeting the IL-4/IL-13/STAT-6 pathway for the treatment of asthma".
Prieto and Richter, 2013, Curr Gastroenterol Rep 15:324, "Eosinophilic Esophagitis in Adults: an Update on Medical Management".
Prussin, et al., 2009, J Allergy Clin Immunol. 124(6):1326-1332, "Eosinophilic gastrointestinal disease and peanut allergy are alternatively associated with IL-5+ and IL-5− TH2 responses".
Rayapudi, et al., 2010, Journal of Leukocyte Biology 88, "Indoor insect allergens are potent inducers of experimental eosinophilic esophagitis in mice".
Receptos, Inc. 2013 Annual Report.
Rothenberg, 2004, J Allergy Clin Immunol, "Eosinophilic gastrointestinal disorders (EGID)".
Rothenberg, 2009, Gastroenterology 137:1238-1249, "Biology and Treatment of Eosinophilic Esophagitis".
Stein, et al., 2006, J Allergy Clin Immunol 118(6):1312-1319, "Anti-IL-5 (mepolizumab) therapy for eosinophilic esophagitis".
Strauman, 2009, Immunol Allergy Clin N Am 29, pp. 11-18, "Clinical Evaluation of the Adult who has Eosinophilic Esophagitis".
Straumann, et al., 2001, J Allergy Clin Immunol 108(6):954-961, "Idiopathic eosinophilic esophagitis is associated with a $T_H2$-type allergic inflammatory response".
Straumann, 2005, J Allergy Clin Immunol 115(2):418-419, "Eosinophilic esophagitis: Escalating epidemiology?".
Straumann, et al., 2009 Gut, "Anti-interleukin-5 antibody treatment (mepolizumab) in active eosinophilic oesophagitis: a randomized, placebo-controlled, double-blind trial".
Veerappan, et al., 2009, Clinical Gastroenterology and Hepatology 7:420-426, "Prevalence of Eosinophilic Esophagitis in an Adult Population Undergoing Upper Endoscopy: A Prospective Study".
Wang and Liu, 2008, Current Opinion in Immunology 20:697-702, "The IL-17 cytokine family and their role in allergic inflammation".
Weinbrand-Goichberg, et al., 2013, Immunol Res, "Eosinophilic esophagitis: an immune-mediated esophageal disease".
Wershil, 2009, Immunol Allergy Clin N Am 29, pp. 189-195. "Exploring the Role of Mast Cells in Eosinophilic Esophagitis".
Wilhelm and Stockinger, 2011, Frontiers in Immunology 2(68), "Innate lymphoid cells and type 2 (Th2) mediated immune responses-pathogenic or beneficial?".
Wills-Karp and Finkelman, 2008, Science Signaling 1(51), "Untangling the Complex Web of IL-4 and IL-13 Mediated Signaling Pathways".
Zuo, et al., 2010, Journal of Immunology 185:660-669, "IL-13 Induces Esophageal Remodeling and Gene Expression by an Eosinophil-Independent, IL-13R{alpha}2-Inhibited Pathway".
Otani et al., (2013) Journal of Allergy and Clinical Immunology 131(6):1576-1582, "Anti-IL-5 therapy reduces mast cell and IL-9 cell numbers in pediatric patients with eosinophilic esophagitis".
Kostic et al., (2010) Clinical Immunology 135:S105-S106, "A Fully Human IL4Rα Antibody for Inhibition of IL-4/IL-13-driven TH2 Responses in Allergic Disease".
Wenzel et al., (2013) New England Journal of Medicine 368(26):2455-2466, "Dupilumab in Persistent Asthma with Elevated Eosinophil Levels".
Stone et al., (2008) Clinical & Experimental Allergy 38(12):1858-1865, "Immunomodulatory therapy of eosinophil-associated gastrointestinal diseases".
Nguyen et al., (2011) Immunological Reviews 242(1):258-271, "Immune modulation for treatment of allergic disease".
Mannon et al., (2012) Gut 61(12):1765-1773, "Interleukin 13 and its role in gut defense and inflammation".
International Search Report and the Written Opinion dated Oct. 2, 2014 for corresponding International application No. PCT/US2014/046170.

(56) References Cited

OTHER PUBLICATIONS

Balint and Larrick (1993) Gene 137:109-118, "Antibody engineering by parsimonious mutagenesis".
Carter (2006) The Journal of Immunology 6:343-357, "Potent Antibody Therapeutics by Design".
Corren et al. (2010) American Journal of Respiratory and Critical Care Medicine 181(8): 788-796, "A Randomized, Controlled, Phase 2 Study of AMG 317, an IL-4R Antagonist, in Patients with Asthma.".
Davies, et al. (1996) Immunotechnol. 2(3): 169-179, "Affinity improvement of single antibody VH domains: residues in all three hypervariable regions affect antigen binding".
Davis (2004) Seminars in Immunology 16: 239-243, "The evolutionary and structural 'logic' of antigen receptor diversity".
Gavett, et al. (1997) the American Physiological Society L253-L261, "Interleukin-4 receptor blockade prevents airway responses induced by antigen challenge in mice".
Groves, et al. (2007) AERODERM in AD Poster at St. John's Institute of Dermatology, "Inhibition of IL-4 and IL-13 with an IL-4 mutein (Aeroderm) protects against flares in atopic eczema".
Grunewald, et al., 1998 the Journal of Immunology 160(8):4004-4009, "An Antagonistic IL-4 Mutant Prevents Type I Allergy in the Mouse: Inhibition of the IL-4/IL-13 Receptor System completely Abrogates Humoral Immune Response to Allergen and Development of Allergic Symptoms in Vivo".
Hijnen, et al. (2004) J. Allergy Clin. Immunology 113(2): 334-340, "Serum thymus and activation-regulated chemokine (TARC) and cutaneous T Cell-attracting chemokine (CTACK) levels in allergic diseases: TARC and CTACK are disease-specific markers for atopic dermatitis".
Holt, et al. (2003) Trends Biotechnol. 21 (11): 484-490, "Domain antibodies: proteins for therapy".
Jahnz-Rozyk, et al. (2005) Allergy 60: 685-688, "Serum thymus and activation-regulated chemokine, macrophage-derived chemokine and eotaxin as marker of severity of atopic dermatitis".
Junttila, et al. (2008) J. Exp. Med. 205(11): 2595-2608, "Tuning sensitivity to IL-4 and IL-13: differential expression of IL-4R$\alpha$, IL-13R$\alpha$1, and $\Upsilon$c regulates relative cytokine sensitivity".
Kagami, et al. (2003) Clin. Exp. Immunology 134: 309-313, "Significant elevation of serum levels of eotaxin-3/CCL26, but not of eotaxin-2/CCL24, in patients with atopic dermatitis: serum eotaxin-3/CCL26 levels reflect the disease activity of atopic dermatitis".
Kakinuma, et al. (2002) Clin. Exp. Immunol 127:270-273, "Serum macrophage-derived chemokine (MDC) levels are closely related with the disease activity of atopic dermatitis".
Kakinuma, et al. (2001) J. Allergy Clin. Immunol. 107(3):535-541, "Thymus and activation-regulated chemokine in atopic dermatitis: Serum thymus and activation-regulated chemokine level is closely related with disease activity".
Kakkar, et al. (2011) Pharmaceutical Research, Kluwer Academic Publishers-Plenum Publishers 28(10): 2530-2542, "Population PK and IgE Pharmacodynamic Analysis of a Fully Human Monoclonal Antibody Against IL4 Receptor".
Kopf, et al. (1993) Letters to Nature 362: 245-248, "Disruption of the murine IL-4 gene blocks Th2 cytokine responses".
Kulis, et al. (2011) J. Allergy Clin Immunol 127: 81-88, "Single-tree nut immunotherapy attenuates allergic reactions in mice with hypersensitivity to multiple tree nuts".
Leung, et al. (2003) The New England Journal of Medicine 348:986-993, "Effect of Anti-IgE Therapy in Patients with Peanut Allergy".
Leung, et al. (2004) The Journal of Clinical Investigation 113(5): 651-657, "New insights into atopic dermatitis".
Ludmila et al., 2014 World Allergy Organization Journal 7(1):P8, "Poster 1013: IL-4R alpha antibody inhibits IgE production and airway remodeling in mouse model of house dust mite-induced eosinophilic asthma".
Maliszewski, et al. (1994) Proc. Soc. Exp. Biol. Med. 206(3): 233-237, "In vivo biological effects of recombinant soluble interleukin-4 receptor".

Morioka et al. (Br. J. Dermatol. Jun. 2009; 160 (6): 1172-9).
Nadeau, et al. (2011) J. Allergy Clin. Immunol 127(6) Letters to the Editor, "Rapid oral desensitization in combination with omalizumab therapy in patients with cow's milk allergy".
Ohno, et al. (1985) Proc. Natl. Acad. Sci. USA 82: 2945-2949, "Antigen-binding specificities of antibodies are primarily determined by seven residues of $V_H$".
Ong (2012) Expert Opinion on Emerging Drugs 17:2:129-133, "Editorial update on emerging treatments of atopic dermatitis".
Oyoshi, et al. (2005) Advances in Immunology 102:135-226, "Cellular and Molecular Mechanisms in Atopic Dermatitis".
Peserico, et al. (2008) British Journal of Dermatology 158: 801-807, "Reduction of relapses of atopic dermatitis with methylprednisolone aceptonate cream twice weekly in addition to maintenance treatment with emollient: a multicentre, randomized, double-blind, controlled study".
Rafi, et al. (2010) Allergy and Asthma Proceedings 31(1): 76-83, "Effects of omalizumab in patients with food allergy".
Roitt, et al. (2001) Mosby—Harcourt Publishers Limited, "Immunology—Sixth Edition" pp. 110-111.
Roll, et al. (2006) J. Investig Allergol Clin Immunol 16(2): 79-85, "Safety of specific immunotherapy using a four-hour ultra-rush induction scheme in bee and wasp allergy".
"Sanofi and Regeneron Report Positive Proof-of-Concept Data for Dupilumab, an IL-4R alpha Antibody, in Atopic Dermatitis" 71st Annual Meeting of the American Academy of Dermatology (2013) http://files.shareholder.com/downloads/REGN/2689212012x0x640531/794a7e54-6904-416b-ba38-a4ccc1726852/REGN_News_2013_3_2_General_Releases.pdf.
Sampson, et al. (2011) J. Allergy Clin Immunol. 127(5) Letters to the Editor, "A phase II, randomized, double-blind, parallel-group, placeboOcontrolled oral food challenge trial of Xolair (omalizumab) in peanut allergy".
Sato, et al. (1993) J. Immunol. 150(7): 2717-2723, "Recombinant soluble murine IL-4 receptor can inhibit or enhance IgE responses in vivo".
Schmitt, et al. (2007) J. of Allergy and Clinical Immunology 120(6): 1389-1398, "What are the best outcome measurements for atopic eczema? A systematic review".
Schneider, et al. (2013) J. Allergy Clin Immunol 132(6): 1368-1374, "A pilot study of omalizumab to facilitate rapid oral desensitization in high-risk peanut-allergic patients".
Schmidt-Weber (2012) Chem Immunol Allergy 96: 120-125, "Anti-IL-4 as a New Strategy in Allergy".
Spirin (1986) Vysshaya shkola, Moscow, pp. 17-23, "Molecular Biology Ribosome structure and protein biosynthesis".
Tazawa, et al. (2004) Arch Dermatol Res 295:459-464, "Relative importance of IL-4 and IL-13 in lesional skin of atopic dermatitis".
Tomkinson et al. (2001) J. Immunol 166: 5792-5800, "A Murine IL-4 Receptor Antagonist that Inhibits IL-4- and IL-13-induced Responses Prevents Antigen-Induced Airway Eosinophilia and Airway Hyperresponsiveness".
Vestergaard, et al. (2000) The Journal of Investigative Dermatology 115(4): 640-646, "A Th$_2$ Chemokine, TARC, Produced by Keratinocytes May Recruit CLA$^+$CCR4$^+$ Lymphocytes into Lesional Atopic Dermatitis Skin".
Walker, et al. (1993) Clinical and Experimental Allergy 23:145-153, "Atopic dermatitis: correlation of peripheral blood T cell activation, eosinophilia and serum factors with clinical severity".
Wark, et al. (2006) Advanced Drug Delivery Reviews 58:657-670, "Latest technologies for the enhancement of antibody affinity".
Weihrauch, et al. (2005) Cancer Research 65:5516-5519, "Elevated Serum Levels of CC Thymus and Activation-Related Chemokine (TARC) in Primary Hodgkin's Disease: Potential for a Prognostic Factor".
Whalley, et al. (2004) British Journal of Dermatology 150: 274-283, "A new instrument for assessing quality of life in atopic dermatitis: international development of the Quality of Life Index for Atopic Dermatitis (QoLIAD)".
Yamanaka et al. (Curr. Probl. Dermatol. 2011; 41: 80-92).

(56) References Cited

OTHER PUBLICATIONS

Zurawski, et al. (1995) J. Biol. Chem. Am. Society of Biolochemical Biologists. 270(23):13869-13878, "The primary binding subunit of the human lnterleukin-4 receptor is also a component of the lnterleukin-13 receptor".

Ring, et al., J. Eur. Acad. Dermatol. Venereol. 26(8) 1045-1060, "Guidelines for treatment of atopic eczema (atopic dermatitis) Part 1".

Arron et al. (2009) Am. J. Respir. Crit. Care Med. Online Abstracts Issue. 2009, B21 Airway Inflammation: New Information about Mediators and Biomarkers/Poster Discussion/Monday, May 18, 2009 "Peripheral Biomarkers of an IL-13 Induced Bronchial Epithelial Gene Signature in Asthma".

Bachert et al. (2005) Drugs 65(11):1537-1552 "Pharmacological management of nasal polyposis".

Bateman et al. (2004) Am. J. Respir. Crit. Care Med. 170:836-844 "Can guideline-defined asthma control be achieved?".

Beck et al. (2014) New England Journal of Medicine 371(2): 130-139 "Dupilumab treatment in adults with moderate-to-severe atopic dermatitis".

Burmeister-Getz et al. (2009) J. Clin. Pharmacol. 49:1025-1036 "Human pharmacokinetics/pharmacodynamics of an interleukin-4 and interleukin-13 dual antagonist in asthma".

Cheng et al. (2012) Am J Physiol Gastrointest Liver Physiol 303:G1175-G1187 "Tissue remodeling in eosinophilic esophagitis".

Foote and Winter (1992) J. Mol. Biol. 224:487-499 "Antibody Framework Residues Affecting the Conformation of the Hypervariable Loops".

Gevaert et al. (2006) Journal of Allergy and Clinical Immunology 118(5):1133-1141 "Nasal IL-5 levels determine the response to anti-IL-5 treatment in patients with nasal polyps".

Hopkins (2009) Clinical Otolaryngology 34(5):447-454 "Psychometric validity of the 22-item Sinonasal Outcome Test".

Kelly and Liu (2014) World Allergy Organization Journal 7(S1):P8 "Poster 1013: IL-4R alpha antibody inhibits IgE production and airway remodeling in mouse model of house dust mite-induced eosinophilic asthma".

Lezcano-Meza et al. (2003) Allergy 58(10):1011-1017 "Interleukin (IL)-4 and to a lesser extent either IL-13 or interferon-gamma regulate the production of eotaxin-2/CCL24 in nasal polyps".

Lin et al (2007) Clinical Reviews in Allergy & Immunology 33(3):167-177 "Role of Bacterial Pathogens in Atopic Dermatitis".

Molfino et al. (2012) Clinical & Experimental Allergy 42(5):712-737 "Molecular and clinical rationale for therapeutic targeting of interleukin-5 and its receptor".

Moldoveanu et al. (2009) Journal of Inflammation Research 2:1-11 "Inflammatory mechanisms in the lung".

Müller et al. (1993) Journal of Immunology 150:5576-5584 "Th2 cells mediate IL-4-dependent local tissue inflammation".

Niederberger (2009) Immunology Letters 122:131-133 "Allergen-specific immunotherapy".

Otulana et al. (2011) Am. J. Respir. Crit. Care Med. 183:A6179 "A Phase 2b Study of Inhaled Pitrakinra, an IL-4R/IL-13 Antagonist, Successfully Identified Responder Subpopulations of Patients with Uncontrolled Asthma".

Petry et al. (2012) Anais Brasileiro De Dermatologica 87(5):732-733 "Bacterial skin colonization and infections in patients with atopic dermatitis".

Sanofi with Regeneron Pharmaceuticals "An Evaluation of Dupilumab in Patients with Nasal Polyposis and Chronic Symptoms of Sinusitis" Trial in Progress, Jun. 2014. ClinicalTrials.gov Identifier: NCT01920893. Retrieved from the Internet URL: http://clinicaltrials.govishow/NCT01920893 Accessed on Sep. 29, 2014.

Scavuzzo et al. (2005) Biomedicine & Pharmacotherapy 59(6):323-9 "Inflammatory mediators and eosinophilia in atopic and non-atopic patients with nasal polyposis".

Sekiya et al. (2002) Allergy 57:173-177 "Increased levels of a TH2-type CC chemokine thymus and activation-regulated chemokine (TARC) in serum and induced sputum of asthmatics".

Stager et al. (2012) Journal of Allergy, Asthma and Immunology 130(2):516-522.e4 "IL-4 Receptor Polymorphisms Predict Reduction in Asthma Exacerbations During Response to an Anti-IL-4 Receptor Antagonist".

Steinke and Borish (2001) Respiratory Research 2(2):1-5 "Th2 cytokines and asthma Interleukin-4: its role in the pathogenesis of asthma, and targeting it for asthma treatment with interleukin-4 receptor antagonists".

Tepper et al. (1990) Cell 52:457-467 "IL-4 Induces Allergic-like Inflammatory Disease and Alters T Cell Development in Transgenic Mice".

Virchow et al. (1994) Lung. 172:313-334 "Cellular and immunological markers of allergic and intrinsic bronchial asthma".

Watson et al. (2011) Allergy, Asthma & Clinical Immunology 7:S4 "Atopic dermatitis".

Wenzel et al. (2007) Lancet 370:1422-1431 "Effect of an interleukin-4 variant on late phase asthmatic response to allergen challenge in asthmatic patients: results of two phase 2a studies".

Wenzel et al. (2010) European Respiratory Society, Annual Congress "ERS—Programme" pp. 3980.

Winter and Harris (1993) Immunology Today 14(6):243-246 "Humanized Antibodies".

Assa'ad, Amal, "What is new in the Treatment of Eosinophilic Eosophagitis?" Clinical and Translational Allergy 2011 (Suppl 1):S69, doi 10.1186/2045-7022-1-S1-S69.

Ivashkin, V. T., et al., "Eosinophilic esophagitis: literature review and description of own survey," RJGHC, 2012, vol. 22, 1, pp. 71-81.

Sanofi/Regeneron Press Release, "Sanofi and Regeneron Report Positive Results with Sarilumab in First Phase 3 Rheumatoid Arthritis Registration Trial", Paris, France and Tarrytown, NY, Nov. 22, 2013, 3 pages.

Almagro et al., "Humanization of antibodies", (2008) Frontiers in Bioscience 13:1619-1633.

Romaniuk, L.I., "Allergen-specific immunotherapy: mechanisms, methods and efficacy", Clinical Immunology, Allergology and Infectology, 2012, special issue, pp. 44-47. (with English translation of the cited portion).

Bagnasco, Diego et al., "A critical evaluation of Anti-IL-13 and Anti-IL-4 Strategies in Severe Asthma", Int. Arch Allergy Immunol 2016; 170: 122-131.

Durham, Andrew L. et al., "Targeted anti-inflammatory therapeutics in asthma and chronic obstructive lung disease", Airway Disease Section, Nat'l. Heart and Lung Institute, Imperial College London, UK, published Aug. 12, 2015, 12 pages.

Hopkins et al. (2007) Otolaryngology-Head and Neck Surgery 137(4):555-561 "The Lund-Mackay staging system for chronic rhinosinusitis: How is it used and what does it predict?".

Martel, Britta C., et al., "Translational animal Models of Atopic Dermatitis for Preclinical Studies," Yale Journal of Biology and Medicine 90 (2017), pp. 389-402.

Silverberg J.I., et al., "Dupilumab treatment induces rapid clinical improvement of itch in patients with moderate-to-severe atopic dermatitis" Paper presented at: American Academy of Dermatology—76th Annual Meeting; Feb. 16-20, 2018; San Diego, CA, USA.

Silverberg J.I., et al., P481, "Dupilumab treatment rapidly improves itch in patients with moderate-to-severe atopic dermatitis" An Allergy Asthma Immunol. 2017;119(suppl 5):S95.

Hamilton, Jennifer D., et al., "Drug evaluation review: Dupilumab in atopic dermatitis," Immunotherapy (2015) 7(10), 1043-1058.

Blauvelt, Andrew, et al., "Long-term management of moderate-to-severe atopic dermatitis with dupilumab and concomitant topical corticosteroids (Liberty Ad Chronos): a 1-year, randomised, double-blinded, placebo-controlled, phase 3 trial," www.thelancet.com, published online May 4, 2016, http://dx.doi.org/10.1016/S0140-6736(17) 31191-1.

Simpson, E.L., et al., "Two Phase 3 Trials of Dupilumab versus Placebo in Atopic Dermatitis," The New England Journal of Medicine, Oct. 1, 2016, DOI: 10.1056/NEJMoa1610020.

Oetjen, Landon K., et al., "Sensory Neurons Co-opt Classical Immune Signaling Pathways to Mediate Chronic Itch," Sep. 21, 2017, Cell 171, 217-228.

Vakharia, Paras P. et al., "Monoclonal Antibodies for Atopic Dermatitis: Progress and Potential", BioDrugs (2017) 31:409-422.

(56) References Cited

OTHER PUBLICATIONS

Ul-Haq, Zaheer et al., "Interleukin-4 receptor signaling and its binding mechanism: A therapeutic insight from inhibito4s tool box", Cytokine & Growth Factor Review 32 (2016) 3-15.

Mueller, Thomas D. et al., "Structure, binding, and antagonists in the IL-4/IL-13 receptor system", Biochimica et Biophysica Acta (2002) 237-250.

Saeki, Hidehisa, Guidelines for Management of Atopic Dermatitis (Advances in Medicine, Special Issue, 2009, vol. 228, No. 1, pp. 75-79, in part) cited in Japanese Patent Application No. 2015-531149.

Simpson, Eric L. et al., "Dupilumab therapy provides clinically meaningful improvement in patient-reported outcomes (PROs): A phase IIb, randomized, placebo-controlled, clinical trial in adult patients with moderate to severe atopic dermatitis (AD)", Journal of the American Academy of Dermatology, Mosby, Inc., US, vol. 75, No. 3, Jun. 4, 2016 (Jun. 4, 2016.

Simpson, Eric L. et al., "Patient burden of moderate to severe atopic dermatitis (AD): Insights from a phase 2b clinical trial of dupilumab in adults," Journal of the American Academy of Dermatology, Mosby, Inc., US, vol. 74, No. 3, Jan. 14, 2016.

Tsianakas, Athanasios et al., "Dupilumab: A Milestone in the Treatment of Atopic Dermatitis," The Lancet, The Lancet Publishing Group, GB vol. 387, No. 10013, Oct. 8, 2015.

Thaci, Diamant et al.: "Efficacy and Safety of Dupilumab in Adults with Moderate-to-Severe Atopic Dermatitis Inadequately Controlled by Topical Treatments: A Randomised, placebo-Controlled, dose-ranging phase 2b trial," The Lancet, The Lancet Publishing Group, GB, vol. 387, No. 10013, Oct. 8, 2015.

Official Action from Russian Federation for RU Appl. No. 2016104400, dated Oct. 6, 2017, translation.

Ivashkin, V. I., et al., "Eosinophilic esophagitis," a textbook for physians, Moscow, "AISPI RAS" JSC, Feb. 14, 2013, pp. 13-21, 57-62.

Bieber, T., et al., "Atopic dermatitis: a candidate for disease-modifying strategy," Allergy 67 (Apr. 12, 2012) 969-975.

Sanofi, "Positive Phase 2a Results of Dupilumab in Asthma in the New England Journal of Medicine," May 21, 2013, Regeneron Pharmaceuticals, Inc.

Wang, et al., "Peanut-induced intestinal allergy is mediated through a mast cell-IgE-FceRI-IL-13 Pathway," Journal of Allergy and Clinical Immunology, 2010, vol. 126, No. 2, 306-316, e1-e12.

Nadeau, et al., "Oral Immunotherapy and Anti-IgE Antibody-Adjunctive Treatment for Food Allergy," Immunology and Allergy clinics of North America, 2012, vol. 32, No. 1, 111-133.

Mathias, et al., IgE-mediated systemic anaphylaxs and impaired tolerance to food antigens in mice with enhanced IL-4 receptor signaling, Journal of Allergy and Clinical Immunology, 2011, vol. 127, No. 3, 795-805, e1-e6.

Burton, et al., "Direct effects of IL-4 on mast cells drive their intestinal expansion and increase susceptibility to anaphylaxis in a murine model of food allergy," Mucosal Immunology, Nov. 14, 2012, doi:10.1038/mi.2012.112.

Akiyama, et al., A Study on Indoor Allergens Measured in Home Environments of Adult-Asthmatic Patients, Study No. 9620, 1-10.

Terui, et al., "Learning from Fungus Allergy in Atopic Dermatitis Patients," Japan J. Med. Mycol, 2000, vol. 41, No. 3, 157-160.

Wong, et al., "Guidelines for the management of atopic dermatitis (eczema) for pharmacists," CPJ/RPC, Sep./Oct. 2017, vol. 150, No. 5.

Highlights of Prescribing Information, DUPIXENT (dupilumab) injection, for subcutaneous use Initial U.S. Approval: 2017, U.S. Food and Drug Administration (FDA), Revised Mar. 2017.

Hong, Judith, et al., "Management of Itch in Atopic Dermatitis," Seminars in cutaneous Medicine and Surgery, vol. 30, No. 2, May 14, 2011, pp. 71-86 XP028240445.

Paton, D. M., "Dupilumab: human monoclonal antibody against IL-4Ralpha for moderate to severe atopic dermatitis," Drugs Today, vol. 53, No. 9, Sep. 1, 2017, pp. 477-487, XP055465888.

Cortes, J. R, et al., Proton pump inhibitors inhibit IL-4 and IL-13 signaling stat6 activation, European Journal of Ummunology, (Sep. 2009) vol. 39, Supp.

Akiyama, et al., A Study on Indoor Allergens Measured in Home Environments of Adult-Asthmatic Patients, Housing Research Foundation, Research Annual Report, 1997, No. 24, Study No. 9620, 1-10.

Dellon, Evan S. et al., "A Randomized, Double-Blind, Placebo-Controlled Trial of a Novel Recombinant, Humanized, Anti-Interleukin-13 Monoclonal Antibody (RPC4046) in Patients with Active Eosinophilic Esophagitis: Results of the HEROES Study", Oct. 14, 2016, retrieved from the Internet on Sep. 20, 2018 at: https://www.eventscribe.com/2016/ACG/QRcode.asp?Pres=178380, 3 pages.

Rothenberg, Marc E. et al., "Intravenous anti-IL-13 mAb QAX576 for the Treatment of eosinophilic esophagitis", Journal of Allergy and Clinical Immunology, vol. 135, No. 2, Feb. 1, 2015, pp. 500-507.

Hirano, Ikuo et al., "Dupilumab Efficacy and Safety in Adult Patients With Active Eosinophilic Esophagitis: a Randomized Double-Blind Placebo-Controlled Phase 2 Trial", Oct. 13, 2017, retrieved from the Internet on Sep. 20, 2018 at: http://files.shareholder.com/downloads/REGN/6138593856x0x959724/16AF93AE-DAF8-480A-8301-311C91E8FA41/Presentation.pdf, 20 pages.

Hirano, Ikuo et al., "Sa1113—Correlation Between Esophageal Distensibility and Objective Measures of Disease in Patients with Active Eosinophilic Esophagitis: A Post HOC Analysis of a Randomized, Placebo-Controlled, Phase 2 Dupilumab Trial", abstract, Gastroenterology, vol. 154, No. 6, May 1, 2018, 1 page.

Collins, Margaret H. et al., "Sa1151—Baseline Characteristics and Correlation Between Dysphagia and Disease Activity in Patients with Eosinophilic Esophagitis in a Randomized, Placebo-Controlled, Phase 2 Dupilumab Trial", abstract, Gastroenterology, vol. 154, No. 6, May 1, 2016, 1 page.

Pesek, Robert D. et al., "Emerging drugs for eosinophilic esophagitis", Expert Opinion on Emerging Drugs, vol. 23, No. 2, Apr. 3, 2018, 12 pages.

European Notice of Opposition in Application 13765844.9, dated Feb. 22, 2019, 34 pages.

Nguyen, Tran Hoai et al., "Future Forms of Immunotherapy and Immunomodulators in Allergic Disease", Immunol Allergy Clin N Am 31 (2011); 343-365.

Antoniu, Sabina, "Pitrakinra, a Dual IL-4R/IL-13 Antagonist for the Potential Treatment of Asthma and Eczema", Current Opinion in Investigational Drugs 2010 11 (11): 1286-1294.

International Investigative Dermatology, Edinburgh, Conference Posters, May 8-11, 2013, 4 pages.

Abstracts, "Human Clinical Research and Therapeutics", Journal of Investigative Dermatology vol. 133, Supplement 1, (2013), pp. S159-S190, Abstracts 1042, and 1048 to 1050, http://apps.webofknowledge.com/full_record.do?product=WOS&search_mode=GeneralSearch&qid=2&SID=E6MDFsiCnXC9MfROx21&page=1&doc=1, 32 pages.

Bankhead, Charles, "IL-4 Antibody Tames Atopic Dermatitis", Medpage Today Article, https://www.medpagetoday.com/meetingcoverage/aad/37636, Mar. 3, 2013, 3 pages.

Clinical Trials, Study NCT01548404—"Study of REGN668 in Adult Patients With Extrinsic Moderate-to-Severe Atopic Dermatitis", first publication of clinical study protocol, Mar. 7, 2012, 7 pages.

Clinical Trials, Study NCT01548404—"Study of Dupilumab in Adult Patients with Extrinsic Moderate-to-severe Atopic Dermatitis", final publication of clinical study protocol, Aug. 27, 2015, 8 pages.

Clinical Trials, Study NCT00676884—"A Phase Study to Investigate the Effects of Repeated Administration of AeroDerm in Subjects with Atopic Dermatitis", Aeroderm first publication of clinical study protocol in TCS resistant moderate-to-severe AD, May 13, 2008, 6 pages.

Garrig, A., "71st Annual Meeting of the American Academy of Dermatology (AAAD) . . . Miami Beach, FL, Mar. 1-5, 2013", Drugs of the Future 2013, 38(4): 275-279, Apr. 2013, https://journals.

(56) References Cited

OTHER PUBLICATIONS prous.com/journals/servlet/xmlxls/ok_journals.xml_toc_pr?p_JournalID=2&p_IssueID=1186, 5 pages.
British Society for Allergy and Clinical Immunology (BSACI) Abstracts of the 2013 Annual Meeting (dated Jul. 8-10, 2013), Clinical & Experimental Allergy, 43, 1428-1472, Nov. 22, 2013, https://onlinelibrary.wiley.com/toc/13652222/2013/43/12, 45 pages.
Clinical Trials, Study NCT01639040—"Study to Assess the Safety of REGN668 (SAR231893) Administered Concomitantly with Topical Corticosteroids (TCS) in Patients with Moderate-to-severe Atopic Dermatitis (AD)", concomitant treatment with TCS, Jul. 11, 2012, 6 pages.
Journal of Allergy & Clinical Immunology: Abstracts at conference; https://www.jacionline.org/issue/S0091-6749(13)X0013-2, Feb. 2013, 1 page.
Joost, T.H. Van, "Cyclosporin in atopical dermatitis: a multicentre placebo-controlled study", Journal of the America Academy of Dermatology, (1992), vol. 27, Issue 6, Part 1, pp. 922-928.
BSACI News Report confirming BSACI conference date of Jul. 8-10, 2013, 2 pages.
ClinicalTrials.gov Identifier: NCT01312961, "Efficacy, Safety, and Tolerability of Dupilumab in Patients with Persistent Moderate to Severe Eosinophilic Asthma" NIH U.S. National Library of Medicine, Mar. 11, 2011.
Regeneron 2011 Annual Report (Apr. 2011), 12 pages.
ClinicalTrials.gov archive, History of Changes for Study: NCT01548404, "Study of Dupilumab in Adult Patients with Extrinsic Moderate-to-Severe Atopic Dermatitis", (Apr. 19, 2012), 7 pages.
ClinicalTrials.gov archive, History of Changes for Study: NCT01259323, "Sequential Ascending Dose Study to Assess the Safety and Tolerability of REGN668 (SAR231893) in Patients With Atopic Dermatitis", (May 31, 2012), 6 pages.
Regeneron: "Highlights of Prescribing Information See 17 for Patient Counseling Information and FDA-approved patient labeling. Revised: Mar. 2017 Full Prescribing Information: Contents 1 Indications and Usage 2 Dosage and Administration 2.1 Dosage 2.2 Important Administration Instructions 2.3 Preparation for Use", (Apr. 7, 2017), XP055534130, Retrieved from the Internet: URL: https://web.archive.org/web/20170407151633if_/https://www.regeneron.com/sites/default/files/Dupixent_FPI.pdf, 4 pages.
Huang, Evie et al: "Severe Atopic Dermatitis in Children", Current Allergy and Asthma Reports, Current Science, US, vol. 18, No. 6, May 10, 2018, pp. 1-8.
Akinlade, B. et al: "Conjunctivitis in dupilumab clinical trials", British Journal of Dermatology, (Mar. 9, 2019), pp. 1-15.
Regeneron: "Dupixent: Highlights of Prescribing Information", (Mar. 1, 2019), pp. 1-8, XP55610296, URL: https://dlegnxy4jxlq3f.cloudfront.net/Regeneron/Dupixent_FPI.pdf, 8 pgs.
Paller et al: "Early and sustained, clinically meaningful responses with dupilumab treatment in a phase 3 trial in adolescents with moderate-to-severe atopic dermatitis", Pediatric Dermatology, vol. 36, No. Suppl. 1, (Apr. 29, 2019), p. S4.
Database Embase [Online], Elsevier Science Publishers, Amsterdam,NL; (May 1, 2019), Cork M. J.:"605 Efficacy and safety of dupilumab in adolescent patients with moderate-to-severe atopic dermatitis", XP002793331, Database accession No. EMB-002001809007 abstract, 3 pages.
Database Embase [Online], Elsevier Science Publishers, Amsterdam,NL; (May 1, 2019), Paller, A.S.:"621 Dupilumab in adolescents with moderate-to-severe atopic dermatitis and a history of inadequate response, or intolerance to cyclosporine: subgroup analysis from a pivotal 16-week trial", XP002793332, Database accession No. EMB-002001808313, Abstract, 2 pages.
Kopp, M.V. et al., "Combination of omalizumab and specific immunotherapy is superior to immunotherapy in patients with seasonal allergic rhinoconjunctivitis and co-morbid seasonal allergic asthma", Clinical and Experimental Allergy, vol. 39, No. 2, pp. 271-279, published on Jan. 22, 2009.
Blanchard, Carine et al., "Eosinophilic esophagitis: Pathogenesis, genetics, and therapy", J. Allergy Clin. Immunol., 2006; 118: 1054-9.
Chan, L.S. et al., "Expression of Interleukin-4 in the epidermis of transgenic mice results in pruritic inflammatory skin disease: an experimental animal model to study atopic dermatitis", J. Invest. Dermatol., 2001, 117: 977-983.
Phan, N.Q. et al., "Assessment of pruritus intensity: prospective study on validity and reliability of the visual analogue scale, numeric rating scale, and verbal rating scale in 471 patients with chronic pruritus", Acta. Derm. Venereol., 2012, 92: 502-507.
Marone et al., "The Intriguing Role of interleukin 13 in the Pathophysiology of Asthma", Frontiers in Pharmacology, 2019, pp. 1-3.
Wegmann et al., "Targeting Cytokines in Asthma therapy: could IL-37 be a Solution?", Expert Review of Respiratory Medicine, 2017, vol. 11, No. 9, pp. 675-677.
Nicodeme et al., "Esophageal Distensibility as a Measure of Disease Severity in Patients with Eosinophilic Esophagitis", Clinical Gastroenterology and Hepatology, 2013, vol. 11, No. 9, pp. 1101-1107.
Straumann et al., "Anti-TNF-a (infliximab) therapy for severe adult eosinophilic esophagitis", J Allergy Clin Immunol, 2008, 122:425-427.

\* cited by examiner

SEQUENCE LISTING

```
<160> NUMBER OF SEQ ID NOS: 14

<210> SEQ ID NO 1
<211> LENGTH: 124
<212> TYPE: PRT
<213> ORGANISM: Artificial Sequence
<220> FEATURE:
<223> OTHER INFORMATION: HCVR

<400> SEQUENCE: 1

Glu Val Gln Leu Val Glu Ser Gly Gly Gly Leu Glu Gln Pro Gly Gly
1               5                   10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
```

```
                    100                 105                 110
Asp Val Trp Gly Gln Gly Thr Thr Val Thr Val Ser
            115                 120

<210> SEQ ID NO 2
<211> LENGTH: 112
<212> TYPE: PRT
<213> ORGANISM: Artificial Sequence
<220> FEATURE:
<223> OTHER INFORMATION: LCVR

<400> SEQUENCE: 2

Asp Ile Val Met Thr Gln Ser Pro Leu Ser Leu Pro Val Thr Pro Gly
1               5                   10                  15

Glu Pro Ala Ser Ile Ser Cys Arg Ser Gln Ser Leu Leu Tyr Ser
            20                  25                  30

Ile Gly Tyr Asn Tyr Leu Asp Trp Tyr Leu Gln Lys Ser Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Thr Pro Tyr Thr Phe Gly Gln Gly Thr Lys Leu Glu Ile Lys
                100                 105                 110

<210> SEQ ID NO 3
<211> LENGTH: 8
<212> TYPE: PRT
<213> ORGANISM: Artificial Sequence
<220> FEATURE:
<223> OTHER INFORMATION: HCDR1

<400> SEQUENCE: 3

Gly Phe Thr Phe Arg Asp Tyr Ala
1               5

<210> SEQ ID NO 4
<211> LENGTH: 8
<212> TYPE: PRT
<213> ORGANISM: Artificial Sequence
<220> FEATURE:
<223> OTHER INFORMATION: HCDR2

<400> SEQUENCE: 4

Ile Ser Gly Ser Gly Gly Asn Thr
1               5

<210> SEQ ID NO 5
<211> LENGTH: 18
<212> TYPE: PRT
<213> ORGANISM: Artificial Sequence
<220> FEATURE:
<223> OTHER INFORMATION: HCDR3

<400> SEQUENCE: 5

Ala Lys Asp Arg Leu Ser Ile Thr Ile Arg Pro Arg Tyr Tyr Gly Leu
1               5                   10                  15

Asp Val

<210> SEQ ID NO 6
```

```
<211> LENGTH: 11
<212> TYPE: PRT
<213> ORGANISM: Artificial Sequence
<220> FEATURE:
<223> OTHER INFORMATION: LCDR1

<400> SEQUENCE: 6

Gln Ser Leu Leu Tyr Ser Ile Gly Tyr Asn Tyr
1               5                   10

<210> SEQ ID NO 7
<211> LENGTH: 3
<212> TYPE: PRT
<213> ORGANISM: Artificial Sequence
<220> FEATURE:
<223> OTHER INFORMATION: LCDR2

<400> SEQUENCE: 7

Leu Gly Ser
1

<210> SEQ ID NO 8
<211> LENGTH: 9
<212> TYPE: PRT
<213> ORGANISM: Artificial Sequence
<220> FEATURE:
<223> OTHER INFORMATION: LCDR3

<400> SEQUENCE: 8

Met Gln Ala Leu Gln Thr Pro Tyr Thr
1               5

<210> SEQ ID NO 9
<211> LENGTH: 117
<212> TYPE: PRT
<213> ORGANISM: Artificial Sequence
<220> FEATURE:
<223> OTHER INFORMATION: HCVR-mouse surrogate Ab

<400> SEQUENCE: 9

Glu Val Gln Leu Gln Gln Ser Gly Pro Glu Leu Val Lys Pro Gly Ala
1               5                   10                  15

Ser Val Arg Met Ser Cys Lys Ala Ser Gly Tyr Thr Phe Thr Asp Tyr
            20                  25                  30

Asn Ile His Trp Val Lys Gln Ser His Gly Lys Ser Leu Glu Trp Ile
        35                  40                  45

Gly Tyr Ile Tyr Pro Asn Asn Gly Asp Asn Gly Tyr Asn Gln Lys Phe
    50                  55                  60

Arg Gly Lys Ala Thr Leu Thr Val Asp Lys Ser Ser Thr Ala Tyr
65                  70                  75                  80

Met Glu Leu Arg Ser Leu Thr Ser Asp Asp Ser Ala Val Tyr Tyr Cys
                85                  90                  95

Ala Arg Gly Arg Leu Arg Tyr Phe Asp Val Trp Gly Thr Gly Thr Thr
            100                 105                 110

Val Thr Val Ser Ser
        115

<210> SEQ ID NO 10
<211> LENGTH: 111
<212> TYPE: PRT
<213> ORGANISM: Artificial Sequence
<220> FEATURE:
<223> OTHER INFORMATION: LCVR-mouse surrogate Ab
```

```
<400> SEQUENCE: 10

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
                20                  25                  30

Gly His Ser Phe Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Leu Asp
65                  70                  75                  80

Pro Val Glu Ala Asp Asp Ala Ala Thr Tyr Tyr Cys Gln Gln Tyr Asn
                85                  90                  95

Glu Asp Pro Pro Thr Phe Gly Ser Gly Thr Lys Leu Glu Ile Lys
            100                 105                 110

<210> SEQ ID NO 11
<211> LENGTH: 207
<212> TYPE: PRT
<213> ORGANISM: Human
<220> FEATURE:
<223> OTHER INFORMATION: IL-4Ralpha

<400> SEQUENCE: 11

Met Lys Val Leu Gln Glu Pro Thr Cys Val Ser Asp Tyr Met Ser Ile
1               5                   10                  15

Ser Thr Cys Glu Trp Lys Met Asn Gly Pro Thr Asn Cys Ser Thr Glu
                20                  25                  30

Leu Arg Leu Leu Tyr Gln Leu Val Phe Leu Leu Ser Glu Ala His Thr
            35                  40                  45

Cys Ile Pro Glu Asn Asn Gly Gly Ala Gly Cys Val Cys His Leu Leu
    50                  55                  60

Met Asp Asp Val Val Ser Ala Asp Asn Tyr Thr Leu Asp Leu Trp Ala
65                  70                  75                  80

Gly Gln Gln Leu Leu Trp Lys Gly Ser Phe Lys Pro Ser Glu His Val
                85                  90                  95

Lys Pro Arg Ala Pro Gly Asn Leu Thr Val His Thr Asn Val Ser Asp
            100                 105                 110

Thr Leu Leu Leu Thr Trp Ser Asn Pro Tyr Pro Pro Asp Asn Tyr Leu
    115                 120                 125

Tyr Asn His Leu Thr Tyr Ala Val Asn Ile Trp Ser Glu Asn Asp Pro
130                 135                 140

Ala Asp Phe Arg Ile Tyr Asn Val Thr Tyr Leu Glu Pro Ser Leu Arg
145                 150                 155                 160

Ile Ala Ala Ser Thr Leu Lys Ser Gly Ile Ser Tyr Arg Ala Arg Val
                165                 170                 175

Arg Ala Trp Ala Gln Cys Tyr Asn Thr Thr Trp Ser Glu Trp Ser Pro
            180                 185                 190

Ser Thr Lys Trp His Asn Ser Tyr Arg Glu Pro Phe Glu Gln His
    195                 200                 205

<210> SEQ ID NO 12
<211> LENGTH: 547
<212> TYPE: PRT
<213> ORGANISM: Artificial Sequence
<220> FEATURE:
<223> OTHER INFORMATION: IL13Ra2 - mIgG2a
``` aa 1-311: mouse IL-13Ra2 (E23-S333)
aa 312-314: linker
aa 315-547: mouse IgG2a Fc (E127 - K359)

<400> SEQUENCE: 12

Glu Ile Lys Val Asn Pro Pro Gln Asp Phe Glu Ile Leu Asp Pro Gly
1               5                   10                  15

Leu Leu Gly Tyr Leu Tyr Leu Gln Trp Lys Pro Val Val Ile Glu
            20                  25                  30

Lys Phe Lys Gly Cys Thr Leu Glu Tyr Glu Leu Lys Tyr Arg Asn Val
            35                  40                  45

Asp Ser Asp Ser Trp Lys Thr Ile Ile Thr Arg Asn Leu Ile Tyr Lys
50                      55                  60

Asp Gly Phe Asp Leu Asn Lys Gly Ile Glu Gly Lys Ile Arg Thr His
65              70                  75                  80

Leu Ser Glu His Cys Thr Asn Gly Ser Glu Val Gln Ser Pro Trp Ile
                85                  90                  95

Glu Ala Ser Tyr Gly Ile Ser Asp Glu Gly Ser Leu Glu Thr Lys Ile
                100                 105                 110

Gln Asp Met Lys Cys Ile Tyr Tyr Asn Trp Gln Tyr Leu Val Cys Ser
            115                 120                 125

Trp Lys Pro Gly Lys Thr Val Tyr Ser Asp Thr Asn Tyr Thr Met Phe
130                     135                 140

Phe Trp Tyr Glu Gly Leu Asp His Ala Leu Gln Cys Ala Asp Tyr Leu
145                 150                 155                 160

Gln His Asp Glu Lys Asn Val Gly Cys Lys Leu Ser Asn Leu Asp Ser
                165                 170                 175

Ser Asp Tyr Lys Asp Phe Phe Ile Cys Val Asn Gly Ser Ser Lys Leu
                180                 185                 190

Glu Pro Ile Arg Ser Ser Tyr Thr Val Phe Gln Leu Gln Asn Ile Val
            195                 200                 205

Lys Pro Leu Pro Pro Glu Phe Leu His Ile Ser Val Glu Asn Ser Ile
210                 215                 220

Asp Ile Arg Met Lys Trp Ser Thr Pro Gly Gly Pro Ile Pro Pro Arg
225                 230                 235                 240

Cys Tyr Thr Tyr Glu Ile Val Ile Arg Glu Asp Asp Ile Ser Trp Glu
                245                 250                 255

Ser Ala Thr Asp Lys Asn Asp Met Lys Leu Lys Arg Arg Ala Asn Glu
            260                 265                 270

Ser Glu Asp Leu Cys Phe Phe Val Arg Cys Lys Val Asn Ile Tyr Cys
            275                 280                 285

Ala Asp Asp Gly Ile Trp Ser Glu Trp Ser Glu Glu Cys Trp Glu
290                 295                 300

Gly Tyr Thr Gly Pro Asp Ser Gly Pro Gly Glu Pro Arg Gly Pro Thr
305                 310                 315                 320

Ile Lys Pro Cys Pro Pro Cys Lys Cys Pro Ala Pro Asn Leu Leu Gly
            325                 330                 335

Gly Pro Ser Val Phe Ile Phe Pro Pro Lys Ile Lys Asp Val Leu Met
            340                 345                 350

Ile Ser Leu Ser Pro Ile Val Thr Cys Val Val Val Asp Val Ser Glu
            355                 360                 365

Asp Asp Pro Asp Val Gln Ile Ser Trp Phe Val Asn Asn Val Glu Val
370                 375                 380

His Thr Ala Gln Thr Gln Thr His Arg Glu Asp Tyr Asn Ser Thr Leu

```
              385                 390                 395                 400
    Arg Val Val Ser Ala Leu Pro Ile Gln His Gln Asp Trp Met Ser Gly
                    405                 410                 415

Lys Glu Phe Lys Cys Lys Val Asn Asn Lys Asp Leu Pro Ala Pro Ile
                420                 425                 430

Glu Arg Thr Ile Ser Lys Pro Lys Gly Ser Val Arg Ala Pro Gln Val
                435                 440                 445

Tyr Val Leu Pro Pro Pro Glu Glu Met Thr Lys Lys Gln Val Thr
            450                 455                 460

Leu Thr Cys Met Val Thr Asp Phe Met Pro Glu Asp Ile Tyr Val Glu
    465                 470                 475                 480

Trp Thr Asn Asn Gly Lys Thr Glu Leu Asn Tyr Lys Asn Thr Glu Pro
                    485                 490                 495

Val Leu Asp Ser Asp Gly Ser Tyr Phe Met Tyr Ser Lys Leu Arg Val
                500                 505                 510

Glu Lys Lys Asn Trp Val Glu Arg Asn Ser Tyr Ser Cys Ser Val Val
                515                 520                 525

His Glu Gly Leu His Asn His His Thr Thr Lys Ser Phe Ser Arg Thr
            530                 535                 540

Pro Gly Lys
    545

<210> SEQ ID NO 13
<211> LENGTH: 451
<212> TYPE: PRT
<213> ORGANISM: Artificial Sequence
<220> FEATURE:
<223> OTHER INFORMATION: HC
      aa 1-124: HCVR
      aa 125-451: HC constant

<400> SEQUENCE: 13

Glu Val Gln Leu Val Glu Ser Gly Gly Gly Leu Glu Gln Pro Gly Gly
    1               5                   10                  15

Ser Leu Arg Leu Ser Cys Ala Gly Ser Gly Phe Thr Phe Arg Asp Tyr
                20                  25                  30

Ala Met Thr Trp Val Arg Gln Ala Pro Gly Lys Gly Leu Glu Trp Val
                35                  40                  45

Ser Ser Ile Ser Gly Ser Gly Gly Asn Thr Tyr Tyr Ala Asp Ser Val
                50                  55                  60

Lys Gly Arg Phe Thr Ile Ser Arg Asp Asn Ser Lys Asn Thr Leu Tyr
    65                  70                  75                  80

Leu Gln Met Asn Ser Leu Arg Ala Glu Asp Thr Ala Val Tyr Tyr Cys
                    85                  90                  95

Ala Lys Asp Arg Leu Ser Ile Thr Ile Arg Pro Arg Tyr Tyr Gly Leu
                100                 105                 110

Asp Val Trp Gly Gln Gly Thr Thr Val Thr Val Ser Ser Ala Ser Thr
                115                 120                 125

Lys Gly Pro Ser Val Phe Pro Leu Ala Pro Cys Ser Arg Ser Thr Ser
                130                 135                 140

Glu Ser Thr Ala Ala Leu Gly Cys Leu Val Lys Asp Tyr Phe Pro Glu
    145                 150                 155                 160

Pro Val Thr Val Ser Trp Asn Ser Gly Ala Leu Thr Ser Gly Val His
                    165                 170                 175

Thr Phe Pro Ala Val Leu Gln Ser Ser Gly Leu Tyr Ser Leu Ser Ser
                180                 185                 190
```

```
Val Val Thr Val Pro Ser Ser Leu Gly Thr Lys Thr Tyr Thr Cys
            195                 200                 205

Asn Val Asp His Lys Pro Ser Asn Thr Lys Val Asp Lys Arg Val Glu
210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
            275                 280                 285

Val His Asn Ala Lys Thr Lys Pro Arg Glu Glu Gln Phe Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
            405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
            435                 440                 445

Ser Leu Gly
    450

<210> SEQ ID NO 14
<211> LENGTH: 219
<212> TYPE: PRT
<213> ORGANISM: Artificial Sequence
<220> FEATURE:
<223> OTHER INFORMATION: LC
      aa 1-112: LCVR
      aa 112-219: LC constant

<400> SEQUENCE: 14

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Ile Gly Tyr Asn Tyr Leu Asp Trp Tyr Leu Gln Lys Ser Gly Gln Ser
            35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80
```

-continued

```
Ser Arg Val Glu Ala Glu Asp Val Gly Phe Tyr Tyr Cys Met Gln Ala
                85                  90                  95

Leu Gln Thr Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

METHODS FOR TREATING EOSINOPHILIC ESOPHAGITIS BY ADMINISTERING AN IL-4R INHIBITOR

CROSS-REFERENCE TO RELATED APPLICATIONS

This application is a continuation of U.S. patent application Ser. No. 14/328,336 filed Jul. 10, 2014, now U.S. Pat. No. 9,290,574, entitled "Methods for treating eosinophilic esophagitis by administering an IL-4R inhibitor," which claims the benefit under 35 U.S.C. § 119(e) of U.S. provisional application No. 61/844,978, filed on Jul. 11, 2013, the disclosure of which is herein incorporated by reference in its entirety.

FIELD OF THE INVENTION

The present invention relates to the use of interleukin-4 receptor inhibitors to treat or prevent eosinophilic esophagitis in a subject in need thereof.

BACKGROUND

Eosinophilic esophagitis (EoE) is an emerging disease characterized by esophageal dysfunction and by abnormal eosinophilic inflammation of the esophagus. The typical symptoms of EoE include food refusal, vomiting, heartburn, dysphagia and food impaction which may lead to impaired quality of life. EoE is found to be associated with food allergy in many patients. Some patients may also have concomitant asthma or an atopic disease such as atopic dermatitis, or allergic rhinitis. EoE is currently diagnosed by endoscopy of the esophagus and biopsy of the esophageal tissue to check for eosinophilia. Treatment options are currently limited to allergen withdrawal, diet modification and corticosteroids. Accordingly, an unmet need exists in the art for effective therapeutic approaches without adverse side-effects that prevent or treat eosinophilic esophagitis and prevent relapse.

BRIEF SUMMARY OF THE INVENTION

According to one aspect of the present invention, methods are provided for treating, preventing or ameliorating at least one symptom or indication of eosinophilic esophagitis (EoE) in a subject. The methods according to this aspect of the invention comprise administering a therapeutically effective amount of a pharmaceutical composition comprising an interleukin-4 receptor (IL-4R) inhibitor to a subject in need thereof. In certain embodiments, the subject in need thereof exhibits an allergic reaction to a food allergen or a non-food allergen.

According to another aspect of the present invention, methods are provided for reducing the level of an EoE-associated biomarker in a subject. In certain embodiments, the EoE-associated biomarker is selected from the group consisting of, e.g., circulating or esophagus eosinophils, eotaxin-3, periostin, serum IgE (total and allergen-specific), IL-13, IL-5, serum thymus and activation regulated chemokine (TARC; CCL17), thymic stromal lymphopoietin (TSLP), serum eosinophilic cationic protein (ECP), and eosinophil-derived neurotoxin (EDN). The methods comprise administering a therapeutically effective amount of a pharmaceutical composition comprising an IL-4R inhibitor.

According to another aspect of the present invention, methods are provided for reducing the eosinophilic infiltration of esophagus in a subject in need thereof. In certain embodiments, methods are provided for reducing inflammation in the esophagus. The methods comprise administering a therapeutically effective amount of a pharmaceutical composition comprising an IL-4R inhibitor. In certain embodiments, the eosinophilic infiltration of the esophagus is represented by greater than or equal to about 15 eosinophils per high powered field in the esophagus of the subject in need thereof. In certain embodiments, the number of eosinophils is reduced by about 50% by day 10 following administration of the IL-4R inhibitor.

In certain embodiments, the IL-4R inhibitor is administered in combination with a second therapeutic agent or therapy.

In certain embodiments, the subject in need thereof has a concurrent disease or disorder selected from the group consisting of food allergy, atopic dermatitis, asthma, allergic rhinitis, allergic conjunctivitis and inherited connective tissue disorders.

Exemplary IL-4R inhibitors that can be used in the context of the methods of the present invention include, e.g., small molecule chemical inhibitors of IL-4R or its ligands (IL-4 and/or IL-13), or biological agents that target IL-4R or its ligands. According to certain embodiments, the IL-4R inhibitor is an antibody or antigen-binding protein that binds the IL-4Rα chain and blocks signaling by IL-4, IL-13, or both IL-4 and IL-13. In certain embodiments, the anti-IL-4R antibody or antigen-binding protein comprises the heavy chain complementarity determining regions (HCDRs) of a heavy chain variable region (HCVR) comprising the amino acid sequence of SEQ ID NO: 1 and the light chain CDRs of a light chain variable region (LCVR) comprising the amino acid sequence of SEQ ID NO: 2. One such type of antigen-binding protein that can be used in the context of the methods of the present invention is an anti-IL-4Rα antibody such as dupilumab.

In certain embodiments, the present invention provides use of an antibody or antigen-binding fragment thereof of the invention in the manufacture of a medicament to treat or inhibit or prevent eosinophilic esophagitis in a subject, including humans.

Other embodiments of the present invention will become apparent from a review of the ensuing detailed description.

DETAILED DESCRIPTION

Figure 1:
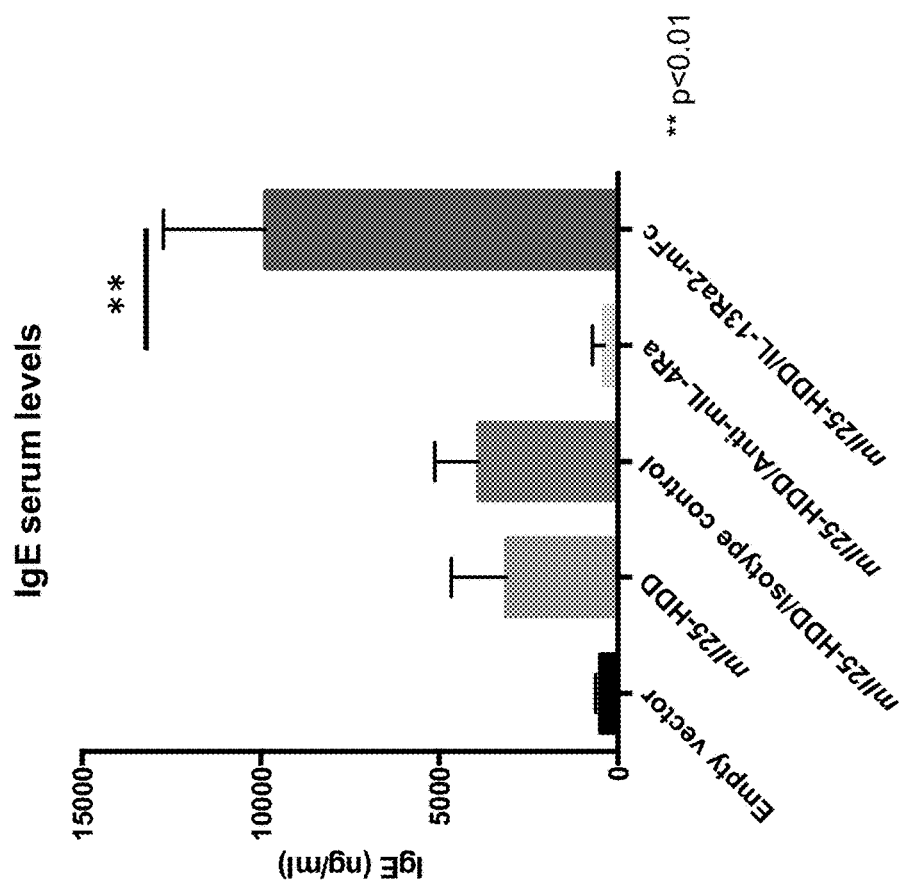
FIG. 1 shows the serum IgE levels in mice injected with Il25 DNA using the hydrodynamic DNA delivery (HDD) method and subsequently treated with the isotype control, anti-mIL-4R mAb or IL-13Ra2-mFc as described in Example 1 herein.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice of the present invention, the preferred methods and materials are now described. All publications mentioned herein are incorporated herein by reference to describe in their entirety.

Methods for Treating, Preventing or Ameliorating Eosinophilic Esophagitis

The present invention includes methods for treating, preventing, or ameliorating at least one symptom or indication of eosinophilic esophagitis (EoE) in a subject. The methods according to this aspect of the invention comprise administering a therapeutically effective amount of a pharmaceutical composition comprising an IL-4R inhibitor to the subject in need thereof. As used herein, the terms "treat", "treating", or the like, mean to alleviate symptoms, eliminate the causation of symptoms either on a temporary or permanent basis, or to prevent or slow the appearance of symptoms of eosinophilic inflammation in the esophagus. In certain embodiments, the present methods are useful for treating or ameliorating at least one symptom or indication of EoE including, but not limited to, eosinophilic infiltration of the esophagus, thickening of the esophageal wall, inflammation in the esophagus, appearance of trachea-like rings or ridges in the esophagus, chest and abdominal pain, food refusal, vomiting, dysphagia and food impaction.

"Eosinophilic Esophagitis" (EoE), as used herein, means an inflammatory disease characterized by abnormal eosinophilic inflammation within the esophagus and esophageal dysfunction. The primary symptoms of EoE include, but are not limited to, chest and abdominal pain, dysphagia, heartburn, food refusal, vomiting and food impaction. The clinicopathology of EoE is characterized by presence of ridges or trachea-like rings in the esophageal wall and eosinophilic infiltration in the esophageal mucosa. EoE is presently diagnosed by endoscopy of the esophagus followed by microscopic and biochemical analysis of the esophageal mucosal lining. EoE may be classified as allergic or non-allergic depending upon the status of the subject. The present invention includes methods to treat both allergic and non-allergic forms of EoE.

As used herein, the expression "a subject in need thereof" means a human or non-human mammal that exhibits one or more symptoms or indications of eosinophilic esophagitis, and/or who has been diagnosed with eosinophilic esophagitis (EoE). In certain embodiments, the methods of the present invention may be used to treat patients that show elevated levels of one or more EoE-associated biomarkers (described elsewhere herein). For example, the methods of the present invention comprise administering an IL-4R inhibitor to patients with elevated levels of IgE or eotaxin-3. The term "a subject in need thereof" may also include, e.g., subjects who, prior to treatment, exhibit (or have exhibited) one or more indications of EoE such as, e.g., esophageal overexpression of pro-inflammatory mediators such as mast cells, eosinophilic infiltration of the esophagus, thickening of the esophageal wall, dysphagia, food impaction and chest and abdominal pain and/or an elevated level of a EoE-associated biomarker. The term also includes subjects who show the presence of 15 eosinophils per high power field in the esophagus, and subjects with elevated peripheral eosinophil counts (>300 cells/µl) or elevated serum IgE (>150 kU/L).

In certain embodiments, the present methods may be used to treat subjects who exhibit pathology and symptoms that are observed in subjects with chronic esophagitis including in gastroesophageal reflux disease (GERD). In certain embodiments, the term "a subject in need thereof" includes subjects that are non-responsive to or resistant to anti-GERD therapy. For example, the present methods may be used to treat subjects that are resistant to proton pump inhibitors (PPI).

In the context of the present invention, "a subject in need thereof" may include a subset of population which is more susceptible to EoE or may show an elevated level of an EoE-associated biomarker. For example, "a subject in need thereof" may include a subject suffering from an atopic disease or disorder such as food allergy, atopic dermatitis, asthma, allergic rhinitis and allergic conjunctivitis. In certain embodiments, the term "a subject in need thereof" includes a subject who, prior to or at the time of administration of the IL-4R inhibitor, has or is diagnosed with a disease or disorder selected from the group consisting of atopic dermatitis, asthma, allergic rhinitis and allergic conjunctivitis. In certain embodiments, the term "a subject in need thereof" may include patients with inherited connective tissue disorders. Such a subject population may show an elevated level of an EoE-associated biomarker such as, e.g., IgE, eotaxin-3, periostin, IL-5, or IL-13.

In certain embodiments, "a subject in need thereof" includes a subject susceptible to an allergen. For example, "a subject in need thereof" includes a subject who may exhibit one of the following characteristics: (a) is prone to allergic reactions or responses when exposed to one or more allergens; (b) has previously exhibited an allergic response or reaction to one or more allergens; (c) has a known history of allergies; and/or (d) exhibits a sign or symptom of an allergic response or anaphylaxis. In certain embodiments, the subject is allergic to an allergen associated with EoE or that renders the subject susceptible and/or prone to developing EoE.

The term "allergen," as used herein, includes any substance, chemical, particle or composition which is capable of stimulating an allergic response in a susceptible individual. Allergens may be contained within or derived from a food item such as, e.g., dairy products (e.g., cow's milk), egg, wheat, soy, corn, rye, fish, shellfish, peanuts and tree nuts. Alternatively, an allergen may be contained within or derived from a non-food item such as, e.g., dust (e.g., containing dust mite), pollen, insect venom (e.g., venom of bees, wasps, mosquitoes, etc.), mold, animal dander, latex, medication, drugs, ragweed, grass and birch.

In certain embodiments, the term "a subject in need thereof" includes a subset of population which exhibits an allergic reaction to a food allergen. For example, "a subject in need thereof" may include a subject who has an allergy to an allergen contained in a food item including, but not limited to, a dairy product, egg, wheat, soy, corn, rye, fish, shellfish, peanut, a tree nut, beef, chicken, oat, barley, pork, green beans, and fruits such as apple and pineapple.

In certain embodiments, the term includes a subject allergic to a non-food allergen such as allergens derived from dust, mold, insects, plants including pollen, and pets such as cats and dogs. Examples of non-food allergens (also known as environmental allergens or aeroallergens) include, but are not limited to, house dust mite allergens, pollen allergens, animal dander allergens, insect venom, grass allergens, and latex.

As used herein, the phrases "allergic response," "allergic reaction," "allergic symptom," and the like, include one or more signs or symptoms selected from the group consisting of urticaria (e.g., hives), angioedema, rhinitis, asthma, vomiting, sneezing, runny nose, sinus inflammation, watery eyes, wheezing, bronchospasm, reduced peak expiratory flow (PEF), gastrointestinal distress, flushing, swollen lips, swollen tongue, reduced blood pressure, anaphylaxis, and organ dysfunction/failure. An "allergic response," "allergic reaction," "allergic symptom," etc., also includes immunological responses and reactions such as, e.g., increased IgE production, increased allergen-specific immunoglobulin production and/or eosinophilia.

In some embodiments, the methods herein may be used to treat EoE in children who are 3 years old. For example, the present methods may be used to treat infants who are less than 1 month, 2 months, 3 months, 4 months, 5 months, 6 months, 7 months, 8 months, 9 months, 10 months, 11 months or less than 12 months old. In other embodiments, the methods of the present invention may be used to treat children who are more than 3 years old, more than 4 years, 5 years, 6 years, 7 years, 8 years, 9 years, 10 years, 11 years, 12 years, 13 years, 14 years, or more than 15 years old.

The present invention also includes methods for reducing eosinophilic infiltration. The methods according to this aspect of the invention comprise administering to the subject one or more doses of a pharmaceutical composition comprising an IL-4R inhibitor to reduce or eliminate the number of eosinophils, e.g., in the esophageal mucosa.

As used herein, "eosinophilic infiltration" refers to the presence of eosinophils in an organ or tissue including blood, esophagus, stomach, duodenum, and ileum of a subject. In the context of the invention, the term "eosinophilic infiltration" refers to presence of eosinophils in the mucosal lining of a region of the gastro-intestinal tract including, but not limited to, esophagus and stomach. Eosinophilic infiltration is analyzed, for example, in an esophageal tissue biopsy of a subject suffering from EoE. According to particular embodiments, "eosinophilic infiltration" refers to the presence of 15 eosinophils per high power field in the esophagus. The term "high power field" refers to a standard total magnification of 400× by a microscope used to view eosinophils in a tissue, e.g., from the esophagus of a subject. In certain embodiments, "eosinophilic infiltration" includes infiltration into a tissue by leucocytes, for example, lymphocytes, neutrophils and mast cells. The leucocyte infiltration into, e.g., esophageal tissue can be detected by cell surface markers such as eosinophil-specific markers (e.g., CD11c$^{Low/Neg}$, SiglecF$^+$, F4/80$^+$, EMR1$^+$, Siglec 8$^+$, and MBP2$^+$), macrophage-specific markers (e.g., CD11b$^+$, F4/80$^+$, CD14$^+$, EMR1$^+$, and CD68$^+$), neutrophil-specific markers (e.g., CD11b$^+$, Ly6G$^+$, Ly6C$^+$, CD11b$^+$, and CD66b$^+$), and T-cell-specific markers (e.g., CD3$^+$ CD4$^+$ CD8$^+$).

As used herein, a reduction in esophagus eosinophils means that the number of eosinophils and other leucocytes measured in the esophagus of a subject with EoE and who has been treated with an IL-4R inhibitor, is at least 5%, 10%, 20%, 50%, 70%, 80%, or 90% lower than the esophagus eosinophils measured in the same or an equivalent subject that has not been treated with the IL-4R inhibitor. In certain embodiments, reducing eosinophilic infiltration means detecting less than 15 eosinophils per high power field, more preferably less than 10 eosinophils, less than 9 eosinophils, less than 8 eosinophils, less than 7 eosinophils, less than 6 eosinophils, or less than 5 eosinophils per high power field in a biopsy of the esophageal mucosa. In certain embodiments, a reduction in esophagus eosinophils means that no eosinophils are detected in the esophageal mucosa of a subject.

The present invention includes methods for treating, preventing or reducing the severity of eosinophilic esophagitis comprising administering a therapeutically effective amount of a pharmaceutical composition comprising an IL-4R inhibitor to a subject in need thereof, wherein the pharmaceutical composition is administered to the subject in multiple doses, e.g., as part of a specific therapeutic dosing regimen. For example, the therapeutic dosing regimen may comprise administering multiple doses of the pharmaceutical composition to the subject at a frequency of about once a day, once every two days, once every three days, once every four days, once every five days, once every six days, once a week, once every two weeks, once every three weeks, once every four weeks, once a month, once every two months, once every three months, once every four months, or less frequently.

The methods of the present invention, according to certain embodiments, comprise administering to a subject a therapeutically effective amount of a pharmaceutical composition comprising an IL-4R inhibitor in combination with a second therapeutic agent. The second therapeutic agent may be an agent selected from the group consisting of, e.g., an IL-1 beta inhibitor, an IL-5 inhibitor, an IL-9 inhibitor, an IL-13 inhibitor, an IL-17 inhibitor, an IL-25 inhibitor, a TNFalpha inhibitor, an eotaxin-3 inhibitor, an IgE inhibitor, a prostaglandin D2 inhibitor, an immunosuppressant, a corticosteroid, a glucocorticoid, a proton pump inhibitor, a decongestant, an antihistamine, and a non-steroidal anti-inflammatory drug (NSAID). In certain embodiments, the IL-4R inhibitor of the invention may be administered in combination with therapy including allergen removal and diet management. As used herein, the phrase "in combination with" means that the pharmaceutical composition comprising an IL-4R inhibitor is administered to the subject at the same time as, just before, or just after administration of the second therapeutic agent. In certain embodiments, the second therapeutic agent is administered as a co-formulation with the IL-4R inhibitor. In a related embodiment, the present invention includes methods comprising administering a therapeutically effective amount of a pharmaceutical composition comprising an IL-4R inhibitor to a subject who is on a background anti-allergy therapeutic regimen. The background anti-allergy therapeutic regimen may comprise a course of administration of, e.g., steroids, antihistamines, decongestants, anti-IgE agents, etc. The IL-4R inhibitor may be added on top of the background anti-allergy therapeutic regimen. In some embodiments, the IL-4R inhibitor is added as part of a "background step-down" scheme, wherein the background anti-allergy therapy is gradually withdrawn from the subject over time (e.g., in a stepwise fashion) while the IL-4R inhibitor is administered the subject at a constant dose, or at an increasing dose, or at a decreasing dose, over time.

Eosinophilic Esophagitis-Associated Biomarkers

The present invention also includes methods involving the use, quantification, and analysis of EoE-associated biomarkers. As used herein, the term "EoE-associated biomarker" means any biological response, cell type, parameter, protein, polypeptide, enzyme, enzyme activity, metabolite, nucleic acid, carbohydrate, or other biomolecule which is present or detectable in an EoE patient at a level or amount that is different from (e.g., greater than or less than) the level or amount of the marker present or detectable in a non-EoE patient. Exemplary EoE-associated biomarkers include, but are not limited to, e.g., esophagus eosinophils, eotaxin-3 (CCL26), periostin, serum IgE (total and allergen-specific), IL-13, IL-5, serum thymus and activation regulated chemokine (TARC; CCL17), thymic stromal lymphopoietin (TSLP), serum eosinophilic cationic protein (ECP), and eosinophil-derived neurotoxin (EDN). The term "EoE-associated biomarker" also includes a gene or gene probe known in the art which is differentially expressed in a subject with EoE as compared to a subject without EoE. For example, genes which are significantly up-regulated in a subject with EoE include, but are not limited to, T-helper 2 (Th2)-associated chemokines such as CCL8, CCL23 and CCL26, periostin, cadherin-like-26, and TNFα-induced protein 6 (Blanchard et al 2006, J. Clin. Invest. 116: 536-547). Alternatively, "EoE-associated biomarker" also includes genes which are down regulated due to EoE such as terminal differentiation proteins (e.g., filaggrin) (Blanchard et al 2006, J. Clin. Invest. 116: 536-547). Certain embodiments of the invention relate to use of these biomarkers for monitoring disease reversal with the administration of the IL-4R antagonist. Methods for detecting and/or quantifying such EoE-associated biomarkers are known in the art; kits for measuring such EoE-associated biomarkers are available from various commercial sources; and various commercial diagnostic laboratories offer services which provide measurements of such biomarkers as well.

According to certain aspects of the invention, methods for treating EoE are provided which comprise: (a) selecting a subject who exhibits a level of at least one EoE-associated biomarker prior to or at the time of treatment which signifies the disease state; and (b) administering to the subject a pharmaceutical composition comprising a therapeutically effective amount of an IL-4R antagonist. In certain embodiments of this aspect of the invention, the subject is selected on the basis of an elevated level of IgE or eotaxin-3.

According to other aspects of the invention, methods for treating EoE are provided which comprise administering to a subject a pharmaceutical composition comprising a therapeutically effective amount of an IL-4R antagonist, wherein administration of the pharmaceutical composition to the subject results in a decrease in at least one EoE-associated biomarker (e.g., esophagus eosinophils, eotaxin-3, IgE, etc.) at a time after administration of the pharmaceutical composition, as compared to the level of the biomarker in the subject prior to the administration.

As will be appreciated by a person of ordinary skill in the art, an increase or decrease in an EoE-associated biomarker can be determined by comparing (i) the level of the biomarker measured in a subject at a defined time point after administration of the pharmaceutical composition comprising an IL-4R antagonist to (ii) the level of the biomarker measured in the patient prior to the administration of the pharmaceutical composition comprising an IL-4R antagonist (i.e., the "baseline measurement"). The defined time point at which the biomarker is measured can be, e.g., at about 4 hours, 8 hours, 12 hours, 1 day, 2 days, 3 days, 4 days, 5 days, 6 days, 7 days, 8 days, 9 days, 10 days, 15 days, 20 days, 35 days, 40 days, 50 days, 55 days, 60 days, 65 days, 70 days, 75 days, 80 days, 85 days, or more after administration of the of the pharmaceutical composition comprising an IL-4R antagonist.

According to certain embodiments of the present invention, a subject may exhibit a decrease in the level of one or more of IgE and/or eotaxin-3 following administration of a pharmaceutical composition comprising an IL-4R antagonist (e.g., an anti-IL-4R antibody). For example, at about day 1, day 4, day 8, day 15, day 22, day 25, day 29, day 36, day 43, day 50, day 57, day 64, day 71 or day 85, following administration of a first, second, third or fourth dose of a pharmaceutical composition comprising about 75 mg to about 600 mg of an anti-IL-4R antibody (e.g., dupilumab), the subject, according to the present invention, may exhibit a decrease in eotaxin-3 of about 1%, 2%, 5%, 10%, 15%, 20%, 25%, 30%, 35%, 40%, 45%, 50%, 55%, 60%, 65%, 70%, 75%, 80%, 85%, 90%, 95% or more from baseline (wherein "baseline" is defined as the level of eotaxin-3 in the subject just prior to the first administration). Similarly, at about day 1, day 4, day 8, day 15, day 22, day 25, day 29, day 36, day 43, day 50, day 57, day 64, day 71 or day 85, following administration of a first, second, third or fourth dose of a pharmaceutical composition comprising about 75 mg to about 600 mg of an anti-IL-4R antibody (e.g., dupilumab), the subject, according to the present invention, may exhibit a decrease in IgE of about 1%, 2%, 5%, 10%, 15%, 20%, 25%, 30%, 35%, 40%, 45%, 50%, 55%, 60%, 65%, 70%, 75%, 80%, 85%, 90%, 95% or more from baseline (wherein "baseline" is defined as the level of IgE in the subject just prior to the first administration).

The present invention also includes methods for determining whether a subject is a suitable subject for whom administration of a pharmaceutical composition comprising an IL-4R antagonist would be beneficial. For example, if an individual, prior to receiving a pharmaceutical composition comprising an IL-4R antagonist, exhibits a level of an EoE-associated biomarker which signifies the disease state, the individual is therefore identified as a suitable patient for whom administration of a pharmaceutical composition of the invention (a composition comprising an anti-IL-4R antibody) would be beneficial. In related embodiments, the present invention includes methods for treating suitable subjects, wherein a suitable subject may be more susceptible to EoE, for example, due to food allergy, or an atopic disease. For example, the present invention includes methods comprising administering an IL-4R antagonist to subjects who have food allergy, atopic dermatitis, asthma, allergic rhinitis or allergic conjunctivitis. In another example, the present invention includes methods comprising administering an IL-4R antagonist to subjects who have, Mendelian-inherited connective tissue disorders, e.g., Marfan syndrome, Loeys-Dietz syndrome, hypermobile Ehlers Danlos syndrome (EDS) or joint hypermobility syndrome (JHS). Such subject populations may have an elevated level of an EoE-associated biomarker.

According to certain exemplary embodiments, an individual may be identified as a good candidate for anti-IL-4R therapy if the individual exhibits one or more of the following: (i) an eotaxin-3 level greater than about 30 pg/ml, greater than about 40 pg/ml, greater than about 50 pg/ml, greater than about 100 pg/ml, greater than about 1500 pg/ml, greater than about 200 pg/ml, greater than about 250 pg/ml, greater than about 300 pg/ml, greater than about 350 pg/ml, greater than about 400 pg/ml, greater than about 450 pg/ml, or greater than about 500 pg/ml; or (ii) a serum IgE level greater than about 114 kU/L, greater than about 150 kU/L, greater than about 500 kU/L, greater than about 1000 kU/L, greater than about 1500 kU/L, greater than about 2000 kU/L, greater than about 2500 kU/L, greater than about 3000 kU/L, greater than about 3500 kU/L, greater than about 4000 kU/L, greater than about 4500 kU/L, or greater than about 5000 kU/L; or (iii) 15 eosinophils per high power field in the esophagus of the subject. Additional criteria, such as other clinical indicators of EoE (e.g., thickening of the esophageal wall, and food allergy indicative of EoE), may be used in combination with any of the foregoing EoE-associated biomarkers to identify an individual as a suitable candidate for anti-IL-4R therapy as described elsewhere herein.

Interleukin-4 Receptor Inhibitors

The methods of the present invention comprise administering to a subject in need thereof a therapeutic composition comprising an interleukin-4 receptor (IL-4R) inhibitor. As used herein, an "IL-4R inhibitor" (also referred to herein as an "IL-4R antagonist," an "IL-4Rα antagonist," an "IL-4R blocker," an "IL-4Rα blocker," etc.) is any agent which binds to or interacts with IL-4Rα or an IL-4R ligand, and inhibits or attenuates the normal biological signaling function a type 1 and/or a type 2 IL-4 receptor. Human IL-4Rα has the amino acid sequence of SEQ ID NO: 11. A type 1 IL-4 receptor is a dimeric receptor comprising an IL-4Rα chain and a γc chain. A type 2 IL-4 receptor is a dimeric receptor comprising an IL-4Rα chain and an IL-13Rα1 chain. Type 1 IL-4 receptors interact with and are stimulated by IL-4, while type 2 IL-4 receptors interact with and are stimulated by both IL-4 and IL-13. Thus, the IL-4R inhibitors that can be used in the methods of the present invention may function by blocking IL-4-mediated signaling, IL-13-mediated signaling, or both IL-4- and IL-13-mediated signaling. The IL-4R inhibitors of the present invention may thus prevent the interaction of IL-4 and/or IL-13 with a type 1 or type 2 receptor.

Non-limiting examples of categories of IL-4R inhibitors include small molecule IL-4R inhibitors, anti-IL-4R aptamers, peptide-based IL-4R inhibitors (e.g., "peptibody" molecules), "receptor-bodies" (e.g., engineered molecules comprising the ligand-binding domain of an IL-4R component), and antibodies or antigen-binding fragments of antibodies that specifically bind human IL-4Rα. As used herein, IL-4R inhibitors also include antigen-binding proteins that specifically bind IL-4 and/or IL-13.

Anti-IL-4Rα Antibodies and Antigen-Binding Fragments Thereof

According to certain exemplary embodiments of the present invention, the IL-4R inhibitor is an anti-IL-4Rα antibody or antigen-binding fragment thereof. The term "antibody," as used herein, includes immunoglobulin molecules comprising four polypeptide chains, two heavy (H) chains and two light (L) chains inter-connected by disulfide bonds, as well as multimers thereof (e.g., IgM). In a typical antibody, each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain (CO). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-IL-4R antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_{H1}$-$C_H2$; (V) $V_H$-$C_{H1}$-$C_{H2}$-$C_H3$; (Vi) $V_H$-$C_{H2}$-$C_H3$; $V_H$-$C_L$; $V_L$-$C_H1$; (ix) $V_L$-$C_H2$; (X) $V_L$-$C_H3$; (xi) $V_L$-$C_{H1}$-$C_H2$; (xii) $V_L$-$C_{H1}$-$C_{H2}$-$C_H3$; (xiii) $V_L$-$C_{H2}$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or heterodimer (or other multimer) of any of the variable and constant domain configurations listed above in non-covalent association with one another and/or with one or more monomeric $V_H$ or $V_L$ domain (e.g., by disulfide bond(s)).

The term "antibody," as used herein, also includes multispecific (e.g., bispecific) antibodies. A multispecific antibody or antigen-binding fragment of an antibody will typically comprise at least two different variable domains, wherein each variable domain is capable of specifically binding to a separate antigen or to a different epitope on the same antigen. Any multispecific antibody format may be adapted for use in the context of an antibody or antigen-binding fragment of an antibody of the present invention using routine techniques available in the art. For example, the present invention includes methods comprising the use of bispecific antibodies wherein one arm of an immunoglobulin is specific for IL-4Rα or a fragment thereof, and the other arm of the immunoglobulin is specific for a second therapeutic target or is conjugated to a therapeutic moiety. Exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^e$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

The antibodies used in the methods of the present invention may be human antibodies. The term "human antibody," as used herein, is intended to include antibodies having variable and constant regions derived from human germline immunoglobulin sequences. The human antibodies of the invention may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

The antibodies used in the methods of the present invention may be recombinant human antibodies. The term "recombinant human antibody," as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

According to certain embodiments, the antibodies used in the methods of the present invention specifically bind IL-4Rα. The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" IL-4Rα, as used in the context of the present invention, includes antibodies that bind IL-4Rα or portion thereof with a $K_D$ of less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. An isolated antibody that specifically binds human IL-4Rα may, however, have cross-reactivity to other antigens, such as IL-4Rα molecules from other (non-human) species.

According to certain exemplary embodiments of the present invention, the IL-4R inhibitor is an anti-IL-4Rα antibody, or antigen-binding fragment thereof comprising a heavy chain variable region (HCVR), light chain variable region (LCVR), and/or complementarity determining regions (CDRs) comprising any of the amino acid sequences of the anti-IL-4R antibodies as set forth in U.S. Pat. No. 7,608,693. In certain exemplary embodiments, the anti-IL-4Rα antibody or antigen-binding fragment thereof that can be used in the context of the methods of the present invention comprises the heavy chain complementarity determining regions (HCDRs) of a heavy chain variable region (HCVR) comprising the amino acid sequence of SEQ ID NO: 1 and the light chain complementarity determining regions (LCDRs) of a light chain variable region (LCVR) comprising the amino acid sequence of SEQ ID NO: 2. According to certain embodiments, the anti-IL-4Rα antibody or antigen-binding fragment thereof comprises three HCDRs (HCDR1, HCDR2 and HCDR3) and three LCDRs (LCDR1, LCDR2 and LCDR3), wherein the HCDR1 comprises the amino acid sequence of SEQ ID NO: 3; the HCDR2 comprises the amino acid sequence of SEQ ID NO: 4; the HCDR3 comprises the amino acid sequence of SEQ ID NO: 5; the LCDR1 comprises the amino acid sequence of SEQ ID NO: 6; the LCDR2 comprises the amino acid sequence of SEQ ID NO: 7; and the LCDR3 comprises the amino acid sequence of SEQ ID NO: 8. In yet other embodiments, the anti-IL-4R antibody or antigen-binding fragment thereof comprises an HCVR comprising SEQ ID NO: 1 and an LCVR comprising SEQ ID NO: 2. In certain embodiments, the methods of the present invention comprise the use of an anti-IL-4R antibody, wherein the antibody comprises a heavy chain comprising the amino acid sequence of SEQ ID NO: 13. In some embodiments, the anti-IL-4R antibody comprises a light chain comprising the amino acid sequence of SEQ ID NO: 14. An exemplary antibody comprising a heavy chain comprising the amino acid sequence of SEQ ID NO: 13 and a light chain comprising the amino acid sequence of SEQ ID NO: 14 is the fully human anti-IL-4R antibody known as dupilumab. According to certain exemplary embodiments, the methods of the present invention comprise the use of dupilumab, or a bioequivalent thereof. The term "bioequivalent", as used herein, refers to anti-IL-4R antibodies or IL-4R-binding proteins or fragments thereof that are pharmaceutical equivalents or pharmaceutical alternatives whose rate and/or extent of absorption do not show a significant difference with that of dupilumab when administered at the same molar dose under similar experimental conditions, either single dose or multiple dose. In the context of the invention, the term refers to antigen-binding proteins that bind to IL-4R which do not have clinically meaningful differences with dupilumab in their safety, purity and/or potency.

In certain particular embodiments, the methods of the present invention comprise the use of an anti-mouse anti-IL-4R antibody or antigen-binding fragment thereof comprising an HCVR sequence of SEQ ID NO: 9 and an LCVR sequence of SEQ ID NO: 10. In an exemplary embodiment, the methods of the present invention comprise the use of an anti-mouse anti-IL-4R antibody ("anti-mIL-4Rα") in reducing eosinophilic infiltration of the esophagus in a mouse model of eosinophilic esophagitis.

Other anti-IL-4Rα antibodies that can be used in the context of the methods of the present invention include, e.g., the antibody referred to and known in the art as AMG317 (Corren et al., 2010, *Am J Respir Crit Care Med.*, 181(8): 788-796), or any of the anti-IL-4Rα antibodies as set forth in U.S. Pat. Nos. 7,186,809, 7,605,237, 7,608,693, or 8,092,804.

The anti-IL-4Rα antibodies used in the context of the methods of the present invention may have pH-dependent binding characteristics. For example, an anti-IL-4Rα antibody for use in the methods of the present invention may exhibit reduced binding to IL-4Rα at acidic pH as compared to neutral pH. Alternatively, an anti-IL-4Rα antibody of the invention may exhibit enhanced binding to its antigen at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding to IL-4Rα at acidic pH as compared to neutral pH" is expressed in terms of a ratio of the $K_D$ value of the antibody binding to IL-4Rα at acidic pH to the $K_D$ value of the antibody binding to IL-4Rα at neutral pH (or vice versa). For example, an antibody or antigen-binding fragment thereof may be regarded as exhibiting "reduced binding to IL-4Rα at acidic pH as compared to neutral pH" for purposes of the present invention if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0, 25.0, 30.0, 40.0, 50.0, 60.0, 70.0, 100.0, or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained. As used herein, the expression "acidic pH" means a pH of 6.0 or less.

Pharmaceutical Compositions

The present invention includes methods which comprise administering an IL-4R inhibitor to a subject wherein the IL-4R inhibitor is contained within a pharmaceutical composition. The pharmaceutical compositions of the invention may be formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262: 4429-4432). Methods of administration include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

In certain situations, the pharmaceutical composition can be delivered in a controlled release system. In one embodiment, a pump may be used. In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Exemplary pharmaceutical compositions comprising an anti-IL-4R antibody that can be used in the context of the present invention are disclosed, e.g., in US Patent Application Publication No. 2012/0097565.

Dosage

The amount of IL-4R inhibitor (e.g., anti-IL-4Rα antibody) administered to a subject according to the methods of the present invention is, generally, a therapeutically effective amount. As used herein, the phrase "therapeutically effective amount" means an amount of IL-4R inhibitor that results in one or more of: (a) a reduction in the severity or duration of a symptom of eosinophilic esophagitis; (b) a reduction in the number of eosinophils in esophagus; (c) prevention or alleviation of an allergic reaction; and (d) a reduction in the use or need for conventional allergy therapy (e.g., reduced or eliminated use of antihistamines, decongestants, nasal or inhaled steroids, anti-IgE treatment, epinephrine, etc.).

In the case of an anti-IL-4Rα antibody, a therapeutically effective amount can be from about 0.05 mg to about 600 mg, e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the anti-IL-4R antibody. In certain embodiments, 300 mg of an anti-IL-4R antibody is administered.

The amount of IL-4R inhibitor contained within the individual doses may be expressed in terms of milligrams of antibody per kilogram of patient body weight (i.e., mg/kg). For example, the IL-4R inhibitor may be administered to a patient at a dose of about 0.0001 to about 100 mg/kg of patient body weight.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Anti-IL-4R Antibody Reduces Eosinophilic Esophagitis in an IL-25-Hydrodynamic DNA Delivery (HDD)-Driven Mouse Model In this Example, the effect of IL-4Rα blockade on eosinophilic esophagitis in an IL25-hydrodynamic DNA delivery (HDD) mouse model was assessed. This model is based on the observation that induced IL-25 expression causes IL-13 signaling via the IL-4Rα/IL-13R heterodimer receptor, and consequently results in eosinophilia of the gastrointestinal tract, including eosinophilic infiltration of the esophagus and mucus production.

On Day 0, Balb/c mice were injected with either a plasmid expressing mouse IL25 DNA ("pRG977/m Il25," n=17), or an empty vector ("pRG977," n=4), each at 25 pg of DNA/mouse by the hydrodynamic DNA delivery (HDD) method (see, e.g., Liu et al. 1999, Gene Therapy 6:1258-1266). The plasmid was diluted in PBS and was injected at a high volume (10% of body weight [ml]), and a high injection rate (6-8 seconds per injection) into the tail vein. Mice that were injected with pRG977/mIl25 DNA were treated by subcutaneous (SQ) injections of either an anti-mouse IL-4R antibody ("anti-mIL-4Rα") or isotype control or a fusion protein of IL-13 receptor alpha unit fused to mouse Fc region ("IL-13Rα2-mFc," used as a decoy receptor; Yasunaga et al 2003; Cytokine 24: 293-303) on Days 1, 3, 6 and 9 each. Each dose was 50 mg/kg of body weight. The anti-mIL-4Rα antibody used in this Example was an antibody comprising an HCVR with an amino acid sequence of SEQ ID NO:9 and an LCVR with an amino acid sequence comprising SEQ ID NO:10. The IL-13Rα2-mFc construct had the amino acid sequence of SEQ ID NO: 12. Mice were euthanized on Day 12 for esophageal and blood analysis. Blood was collected, and serum was used to detect total IgE levels by ELISA.

The esophagus harvested from each mouse was fixed, paraffin embedded and stained with hematoxylin/eosin. Sections were scored for pathology and level of eosinophil infiltration was scored as follows:

Score 0: no changes in esophagus wall thickness, no leukocyte infiltrates;
Score 1: low to moderate leukocyte infiltrates detected in sub-mucosa layer;
Score 2: moderate to severe leukocyte infiltrates in sub-mucosa, detectable thickening of the esophagus wall;
Score 3: severe infiltration of leukocytes resulting marked thickening of the esophagus wall.

The proximal, middle and distal part of each esophagus was evaluated by one score, and the final score per animal was an average of these three values.

Figure 2:
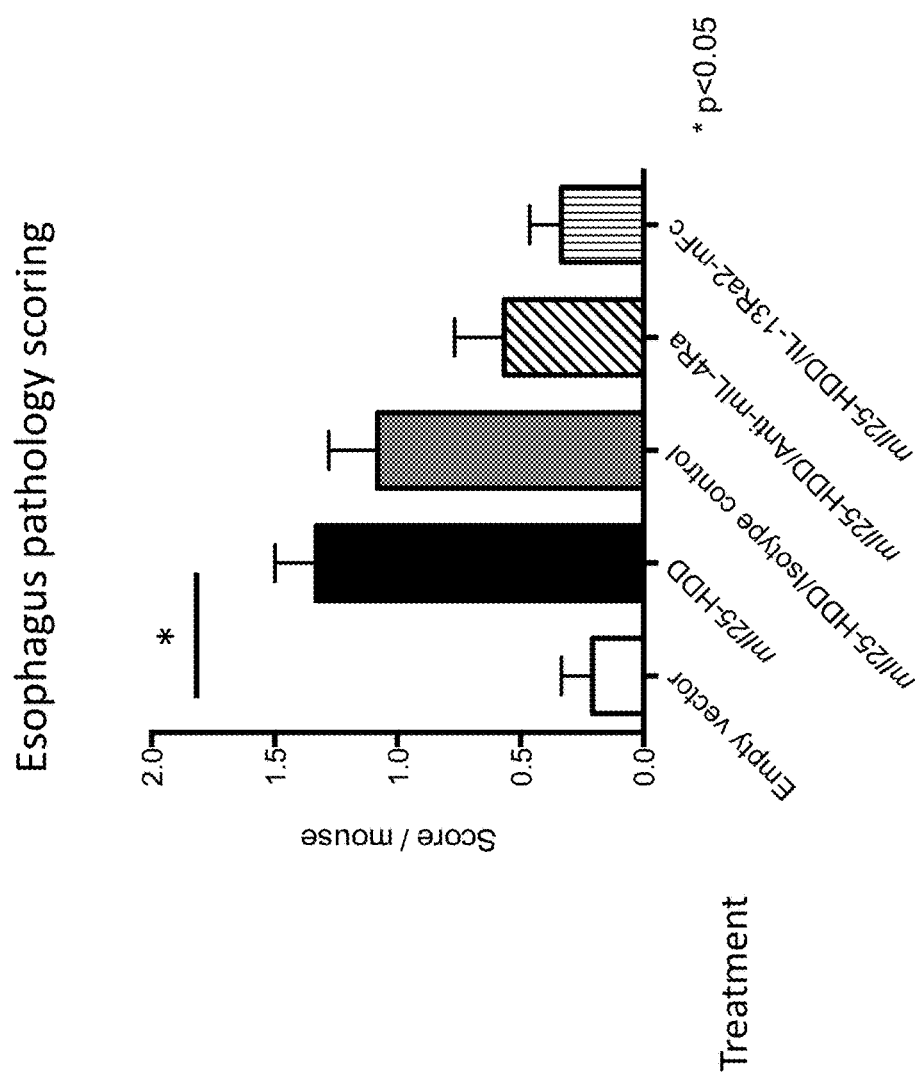
FIG. 2 shows the esophageal histology scores of mice injected with Il25 DNA using the HDD method and subsequently treated with the isotype control, anti-mIL-4R mAb or IL-13Ra2-mFc as described in Example 1 herein.

Mice injected with Il25 and treated with isotype control antibody or IL-13Ra2-mFc fusion protein showed an increased level of serum IgE which was significantly reduced in the mice treated with anti-mIL-4Rα mAb as compared to IL-13Ra2-mFc treatment (see FIG. 1). Histology scoring results are illustrated in FIG. 2. Both anti-mIL-4Rα mAb and IL-13Ra2-mFc reduced the pathology score of the esophagus by about 50% (see FIG. 2). The t-test was used initially to calculate significance; however, ANOVA (or non-parametric Kruskall-Wallis test) was used for later analysis.

Example 2: Anti-IL-4R Antibody Reduces Eosinophilic Infiltration of Esophagus in a Mouse Model of Peanut Allergy In this Example, the effect of IL-4Rα blockade on peanut allergen-induced eosinophilic esophagitis in a mouse model was assessed.

Balb/c mice were sensitized with 200 pg of peanut allergen extract (PAE) in 1 mg of aluminum salts (Alum) adjuvant on day 0 and day 14. Three weeks later, on day 21, mice were challenged intra-nasally with 100 pg of PAE dissolved in 50 μl of phosphate-buffered saline (PBS). The challenge was repeated on day 24, 27 and 30. Starting day 21, one group of challenged mice was not treated and two groups were injected with either anti-IL-4R antibody ("anti-mIL-4R mAb" as described above) at dose 25 mg/kg, or isotype control IgG1. The treatment was applied twice a week, starting day 21. Mice were euthanized 24 hours after the last challenge with PEA on day 31, blood samples and esophagi were collected.

Esophagi were fixed in buffered formalin, paraffin embedded and sectioned slides of tissue were stained with H&E. The extent of leukocyte infiltrates and inflammation was scored in blinded fashion, using following scoring: 0=no changes in esophagus wall thickness, no leukocyte infiltrates; 1=low to moderate leukocyte infiltrates detected in sub-mucosa; 2=moderate to severe leukocyte infiltrates in sub-mucosa, detectable thickening of the esophagus wall; 3=severe infiltration of leukocytes resulting in marked thickening of esophagus wall. Each 25% of the esophagus length received one score (4 scores per esophagus); the average was calculated and used as "score/mouse".

For differential cell count and activity, the esophagus tissue was digested with Liberase DL enzyme for 30 min at 37° C. (n=5 per group). Following Liberase DL digestion, the cell suspension was filtered and cells were stained with eosinophil-, T-cell-, neutrophil-, and macrophage-specific markers and analyzed by flow cytometry. Some of the cells isolated from esophagi by Liberase DL digest were stimulated with anti-CD3 and anti-CD28 antibodies to activate T-cells, and cultured for 3 days. Tissue culture supernatants were assayed by ELISA for levels of Th2 cytokines (IL-13, IL-10, and IL-4).

Figure 3:
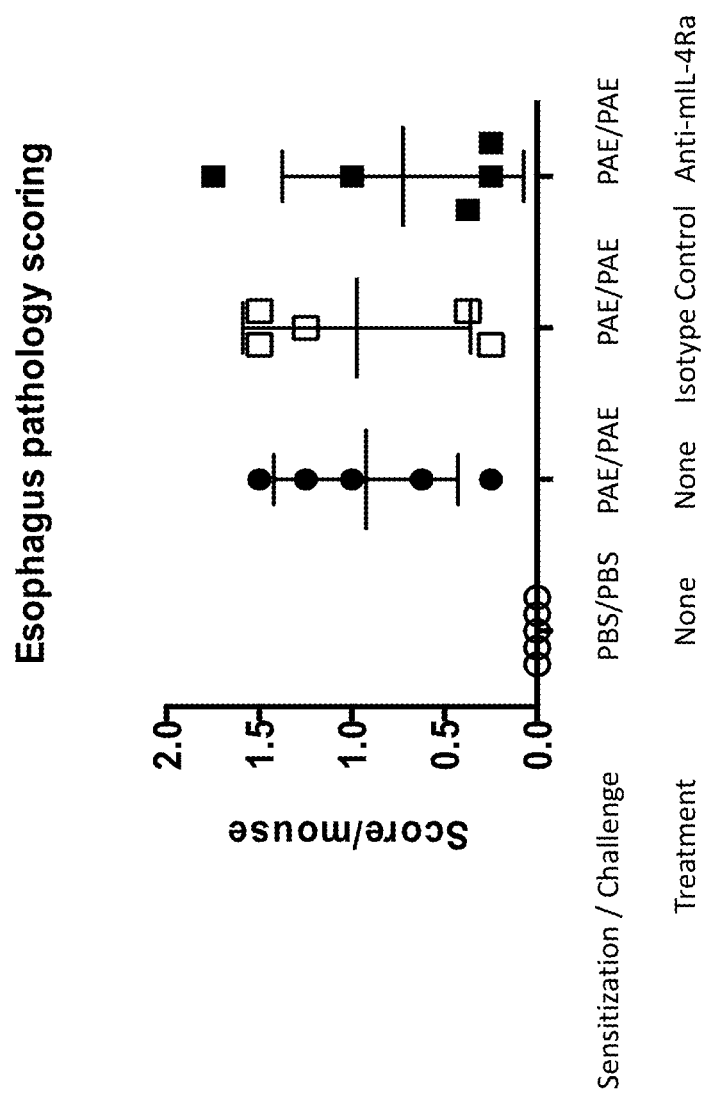
FIG. 3 shows the esophageal histology scores (as described elsewhere herein) of mice sensitized by phosphate-buffered saline (PBS) or by peanut allergen extract (PAE) and challenged by PBS or PAE. The mice were treated with anti-mIL-4R mAb or an isotype control.

The average score for group of mice that was not sensitized & challenged with peanut allergen was 0. Mice that were sensitized & challenged and not treated scored 0.925±0.497 (mean±SD), mice sensitized & challenged and treated with isotype control or anti-mIL-4R mAb scored 0.975±0.615, and 0.725±0.652, respectively. The differences between isotype control—, anti-mIL-4R mAb—or non-treated groups were not statistically significant, according to one-way ANOVA test (shown in FIG. 3).

Blood was also collected by cardiac puncture post-mortem and the serum analyzed for levels of total IgE and peanut-specific IgG1 (PAE-specific IgG1) levels by ELISA. Briefly, for PAE-specific IgG1 detection, PAE-coated plates were incubated with serially diluted serum samples, following by incubation with anti-mouse IgG1-HRP conjugated antibody. The relative levels of IgG1 serum levels were represented as titer units (OD450 was multiplied by a dilution factor required to achieve OD450≤0.5). For detection of total IgE levels, serially diluted serum samples were incubated with anti-IgE capture antibody on 96-well plates and the IgE was detected by biotinylated anti-mouse IgE secondary antibody. Purified mouse IgE that was HRP-labeled was used as a standard.

Figure 4:
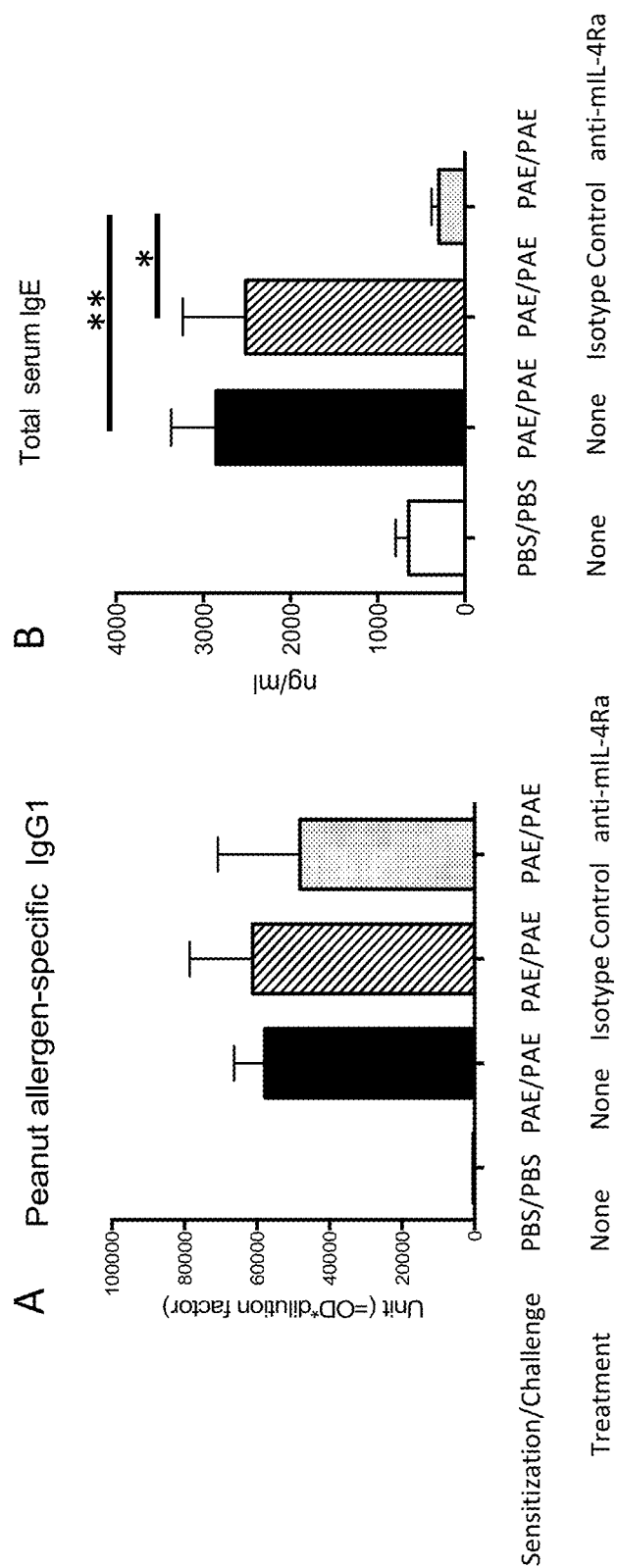
FIGS. 4A and 4B show serum levels of (4A) peanut allergen specific IgG1 and (4B) IgE in mice sensitized by PBS or by peanut allergen extract (PAE) and challenged by PBS or PAE. The mice were treated with anti-mIL-4R mAb or an isotype control.

PAE-specific IgG1 and total IgE levels in blood of non-sensitized & non-challenged mice were 439±17.25 U and 644±337.7 ng/ml, respectively. In PAE sensitized and challenged mice with no additional treatment, the PAE-specific IgG1 and total IgE levels increased to 57822±8455 U, and 2857±1149 ng/ml, respectively. Mice treated with isotype control showed 61304±17293 U of PAE-specific IgG1, and 2516±1613 ng/ml of IgE. Treatment with anti-mIL-4Rα mAb did not significantly affect the PAE-specific level of IgG1 (48128±22691 U) but significantly reduced the total serum level of IgE (300±187.8 ng/ml) as compared to either isotype control-treated, or non-treated mice (shown in FIG. 4).

Example 3: Clinical Trial of Subcutaneously Administered Dupilumab in Adult Patients with Eosinophilic Esophagitis (EoE)

This study is a 32-week, double-blind, randomized, placebo-controlled study to investigate the efficacy, safety, tolerability and immunogenicity of dupilumab in adult patients with EoE. Dupilumab is a fully human anti-IL-4R antibody comprising a heavy chain comprising the amino acid sequence of SEQ ID NO: 13 and a light chain comprising the amino acid sequence of SEQ ID NO: 14; an HCVR/LCVR amino acid sequence pair comprising SEQ ID NOs: 1/2; and heavy and light chain CDR sequences comprising SEQ ID NOs: 3-8.

Study treatment is administered for up to 12 weeks with 16 weeks of safety follow-up. After providing informed consent, eligibility is assessed at the screening visit conducted within 4 weeks of the Day 1 baseline visit. Straumann Dysphagia Instrument (SDI) (0-9) symptom diary data (1 week recall period) and EoE Activity Index (EoEAI) symptom diary data (1 week recall period) are collected during the screening visit and weekly during the study (Straumann et al 2010, Gastroenterology 139: 1526-1537). The Adult EoE Quality of Life Questionnaire is collected at the screening visit and end of treatment visit. Patients who meet eligibility criteria will undergo Day 1 baseline assessments. Patients are randomized in a 1:1 ratio to receive subcutaneous dupilumab 300 mg or placebo once weekly during the 12-week double-blind stage.

Patients 18-50 years of age with a history of a diagnosis of EoE confirmed by documented, peak cell density of ≥15 eos/hpf from esophageal histology biopsy specimens at both proximal and distal levels, a history of at least 2 episodes of dysphagia, and a documented history of, or concomitant allergic asthma, allergic rhinitis, atopic dermatitis, or food allergies; or elevated peripheral eosinophil counts (≥300 cells/μL) or elevated serum IgE (≥150 kU/L) are included in the study.

Study drug treatments include a 600 mg loading dose of dupilumab on day 1, followed by a 300 mg weekly dose; or a placebo double dose on day 1, followed by a weekly placebo dose.

The patients will receive 2 injections (including a loading dose) on day 1, followed by weekly injections. At the end of the 12-week double-blind treatment phase, patients are followed for an additional 16 weeks. The study population is stratified by previous response to swallowed topical corticosteroids use. Inadequate response is defined as failure to normalize tissue eosinophils and resolution of symptoms after at least 2 months of topical therapy. Esophageal biopsies are performed at screening and at week 12. Patients who discontinue the study prior to 12 weeks will have the procedure done at their early termination visit. Measurement of inflammatory and remodeling esophageal features based on EoE Endoscopic Reference Score are included as part of the procedure.

All patients receive concomitant medications (except for prohibited medications) as needed, while continuing study treatment. If necessary, rescue medications (such as systemic and topical corticosteroids) or emergency esophageal dilation will be provided to study patients. Patients receiving rescue therapy are discontinued from the study treatment. Safety, laboratory and clinical effect measurements are performed at specified clinic visits. Post-treatment follow-up visits occur at weeks 16, 20, 24 and 28. Samples for DNA and RNA analysis are collected from patients who enrolled in the optional genomics sub-study. Transcriptome sequencing or microarray analysis of the esophageal biopsy RNA will be performed.

The primary objective of the study is to assess the potential efficacy of repeated weekly subcutaneous doses of dupilumab (12 weeks of treatment) compared to placebo, to control EoE in adult patients with active disease. The secondary objectives are: (a) to assess the safety, tolerability and immunogenicity of repeated subcutaneous doses of dupilumab in adult patients with active EoE; (b) to assess the effect of dupilumab on peak eosinophil counts (eos/hpf) in esophageal biopsies; (c) to evaluate the pharmacokinetics of dupilumab in adult EoE patients; (d) to evaluate and optimize clinical endpoint registration endpoint schema under development; and (e) to assess the pharmacodynamic effect of dupilumab using biomarkers including histology and circulating markers (TARC and eotaxin-3).

The patients are monitored for: (a) percent change in Eosinophilic Esophagitis Activity Index (EoEAI) patient reported outcome from baseline to week 12; (b) change in SDI score from baseline to week 12; and (c) reduction of serum TARC and plasma eotaxin-3 from baseline to week 12. The other endpoints monitored include reduction in esophageal hyperplasia, inflammation, inflammatory gene signature and remodeling (histology), and reduction of esophageal mucosa eosinophil counts per high powered field (400×).

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method of treating or ameliorating at least one symptom or indication of eosinophilic esophagitis (EoE) comprising:
(a) selecting a patient with a history of diagnosis of EoE wherein the patient has ≥15 eosinophils per high powered field (hpf) from a esophageal biopsy specimen; and
(b) administering to the patient one or more doses of a pharmaceutical composition comprising a therapeutically effective amount of an interleukin-4 receptor (IL-4R) inhibitor.

2. The method of claim 1, wherein the symptom or indication of EoE is selected from the group consisting of eosinophilic inflammation of the esophagus, thickening of the esophageal wall, food refusal, vomiting, abdominal pain, heartburn, regurgitation, dysphagia, and food impaction.

3. The method of claim 1, wherein the symptom or indication of EoE is an elevated level of an EoE-associated biomarker.

4. The method of claim 3, wherein the EoE-associated biomarker is selected from the group consisting of eotaxin-3, periostin, serum IgE (total and allergen-specific), IL-13, IL-5, serum thymus and activation regulated chemokine (TARC), thymic stromal lymphopoietin (TSLP), serum eosinophilic cationic protein (ECP), and eosinophil-derived neurotoxin (EDN).

5. The method of claim 1, wherein the patient, prior to or at the time of administration of the pharmaceutical composition, has or is diagnosed with a disease or disorder selected from the group consisting of atopic dermatitis, asthma, allergic rhinitis and food allergies.

6. The method of claim 1, wherein the patient exhibits an allergic reaction to a food allergen contained in a food item selected from the group consisting of a dairy product, egg, wheat, soy, corn, fish, shellfish, peanut, a tree nut, beef, chicken, oat, barley, pork, green beans, apple and pineapple.

7. The method of claim 1, wherein the patient has elevated peripheral eosinophil counts of ≥300 cells/µL.

8. The method of claim 1, wherein the patient has elevated serum IgE level of ≥50 kU/L.

9. The method of claim 1, wherein the pharmaceutical composition is administered subcutaneously to the patient.

10. The method of claim 1, wherein each dose of the pharmaceutical composition comprises 50-600 mg of the IL-4R inhibitor.

11. The method of claim 10, wherein each dose comprises 300 mg of the IL-4R inhibitor.

12. The method of claim 1, wherein step (b) comprises: administering an initial dose of the pharmaceutical composition to the patient; followed by administering one or more subsequent doses of the pharmaceutical composition to the patient, wherein each subsequent dose is administered to the patient one week or two weeks after the immediately preceding dose.

13. The method of claim 12, wherein the initial dose comprises 600 mg and each subsequent dose comprises 300 mg of the IL-4R inhibitor.

14. The method of claim 1, wherein the IL-4R inhibitor is administered in combination with a second therapeutic agent or therapy, wherein the second therapeutic agent or therapy is selected from the group consisting of an IL-1beta inhibitor, an IL-5 inhibitor, an IL-9 inhibitor, an IL-13 inhibitor, an IL-17 inhibitor, an IL-25 inhibitor, a TNFalpha inhibitor, an eotaxin-3 inhibitor, an IgE inhibitor, a prostaglandin D2 inhibitor, an immunosuppressant, a corticosteroid, a glucocorticoid, a proton pump inhibitor, a NSAID, allergen removal and diet management.

15. The method of claim 1, wherein the IL-4R inhibitor is an antibody or antigen-binding fragment thereof that binds IL-4Rα and prevents the interaction of IL-4 and/or IL-13 with a type 1 or type 2 IL-4 receptor.

16. The method of claim 15, wherein the antibody or antigen-binding fragment thereof prevents the interaction of IL-4 with both type 1 and type 2 IL-4 receptors.

17. The method of claim 16, wherein the antibody or antigen-binding fragment thereof comprises the heavy chain complementarity determining regions (HCDRs—HCDR1, HCDR2 and HCDR3) of a heavy chain variable region (HCVR) comprising the amino acid sequence of SEQ ID NO: 1 and the light chain complementarity determining regions (LCDRs—LCDR1, LCDR2 and LCDR3) of a light chain variable region (LCVR) comprising the amino acid sequence of SEQ ID NO: 2.

18. The method of claim 16, wherein HCDR1 comprises the amino acid sequence of SEQ ID NO: 3; HCDR2 comprises the amino acid sequence of SEQ ID NO: 4; HCDR3 comprises the amino acid sequence of SEQ ID NO: 5; LCDR1 comprises the amino acid sequence of SEQ ID NO: 6; LCDR2 comprises the amino acid sequence of SEQ ID NO: 7; and LCDR3 comprises the amino acid sequence of SEQ ID NO: 8.

19. The method of claim 18, wherein the CVR comprises the amino acid sequence of SEQ ID NO: 1 and the LCVR comprises the amino acid sequence of SEQ ID NO: 2.

20. The method of claim 1, wherein the IL-4R inhibitor is dupilumab or a bioequivalent thereof.

* * * * *